United States Patent [19]
Lodzinski

[11] 4,243,319
[45] Jan. 6, 1981

[54] OPTICAL PROPERTY MEASUREMENT SYSTEM AND METHOD

[75] Inventor: Fred P. Lodzinski, Port Edwards, Wis.

[73] Assignee: Nekoosa Papers, Inc., Port Edwards, Wis.

[21] Appl. No.: 761,595

[22] Filed: Jan. 24, 1977

Related U.S. Application Data

[63] Continuation-in-part of Ser. No. 429,637, Dec. 28, 1973, abandoned, said Ser. No. 540,251, said Ser. No. 543,902.

[51] Int. Cl.³ .................. G01N 21/17; G01N 21/86
[52] U.S. Cl. ...................................... 356/73; 356/429
[58] Field of Search ................ 356/73, 199, 200, 429

[56] References Cited

U.S. PATENT DOCUMENTS

| 3,827,808 | 8/1974 | Cho | 356/199 |
| 4,019,819 | 4/1977 | Lodzinski | 356/73 |

FOREIGN PATENT DOCUMENTS 323718  2/1972  U.S.S.R. .................................. 356/200

OTHER PUBLICATIONS

Rutledge, W. C. "Extended Outputs from a System with an On-Line Tristimulus Colorimeter And A Digital Computer", *Tappi* vol. 54, No. 7 Jul. 1971, pp. 1152–1155.

*Primary Examiner*—Vincent P. McGraw
*Attorney, Agent, or Firm*—Hill, Van Santen, Steadman, Chiara & Simpson

[57] ABSTRACT

In an illustrated embodiment, brightness, color, opacity and fluorescent contribution to brightness are measured by an on-line sensing head providing for simultaneous measurement of transmitted and reflected light. By measuring two independent optical parameters, paper optical properties of a partially translucent web are accurately characterized substantially independently of paper grade and weight. The instrument is designed so as to be capable of transverse scanning of a moving paper web on the paper machine, and so as to monitor desired paper optical characteristics with sufficient accuracy to enable on-line control of the optical characteristics of the paper being manufactured.

1 Claim, 6 Drawing Figures

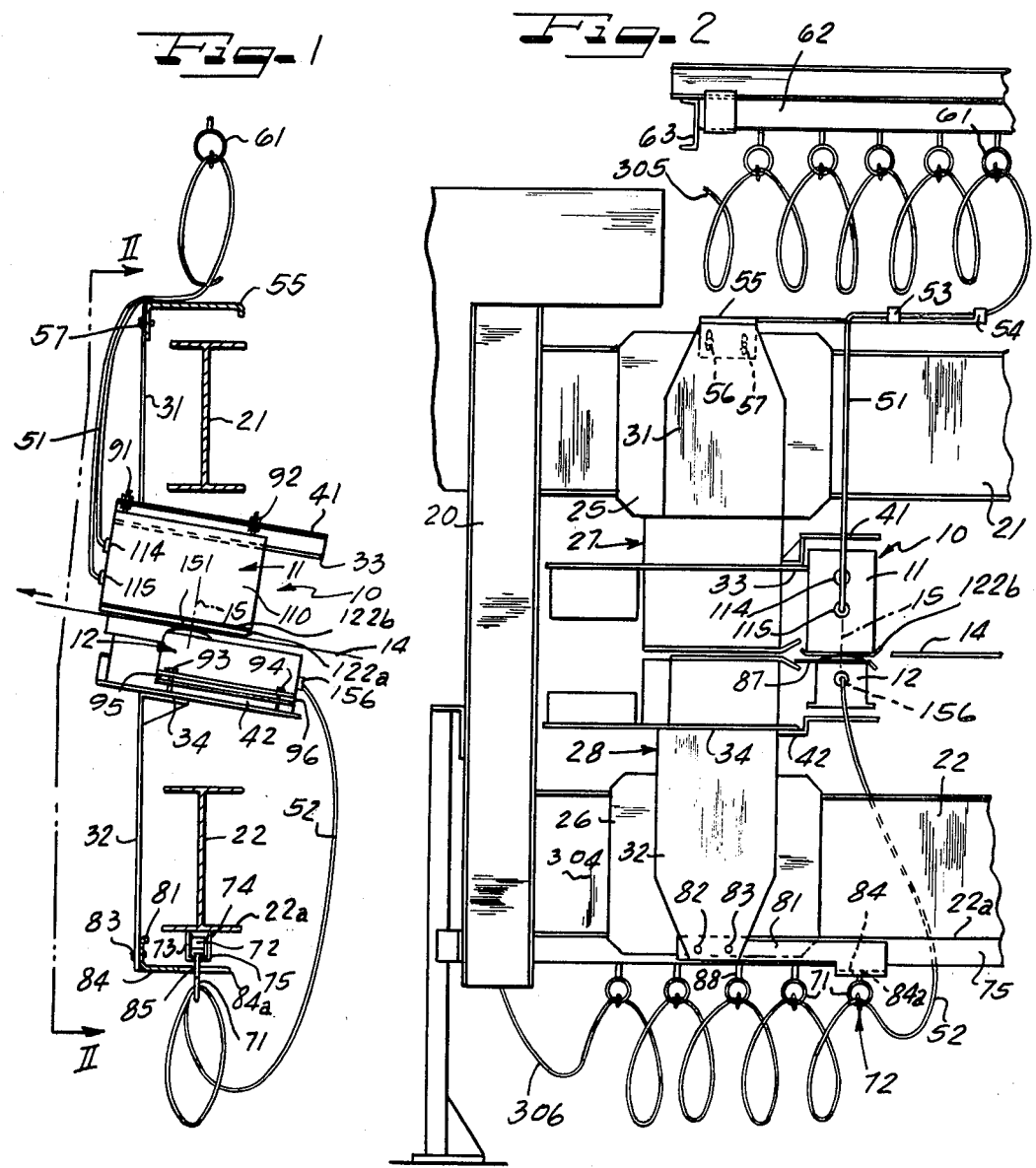

OPTICAL PROPERTY MEASUREMENT SYSTEM AND METHOD

CROSS-REFERENCES TO RELATED APPLICATIONS

The present application is a continuation-in-part of my application Ser. No. 429,637 filed Dec. 28, 1973 (now abandoned) and of my copending applications Ser. No. 540,251 filed Jan. 10, 1975, now U.S. Pat. No. 4,019,819 issued Apr. 26, 1977, and Ser. No. 543,902 filed Jan. 25, 1975, and the written disclosure and drawings of each of these copending applications are incorporated herein by reference in their entireties.

BACKGROUND OF THE INVENTION

In the prior art it is known to obtain an indication of color and brightness characteristics of a paper web during manufacture by an on-line measurement of reflectance value (Rg), but this measurement is decidedly different from that necessary for actual color and brightness characterizations. Accordingly, such a measurement must be accompanied by very frequent off-line testing, so as to enable an adequate empirical calibration of the measuring instrument. Further, a separate set of calibration parameters is required for each grade and weight of paper. Off-line instruments which adequately measure these characteristics require that a pad of several thicknesses of paper be exposed to the light source aperture so that a different reflectance value ($R_\infty$) is obtained. Obviously this is impossible with an on-line instrument unless the far more inaccessible reel itself is tested.

Only where the on-line measured reflectance value (Rg) approaches the off-line value ($R_\infty$), as in instances of paper of extremely high opacity such as heavily coated or heavily dyed paper, can the above problems be minimized to the point where accuracy becomes sufficient for control purposes.

SUMMARY OF THE INVENTION

This invention relates to an optical device and method for sensing optical properties of a paper sheet material, and particularly to an on-the-paper-machine device and method for simultaneously sensing both transmitted and reflected light so as to obtain measurements from which the optical properties of interest can be calculated substantially independently of grade and weight of paper involved.

Accordingly it is an object of the present invention to provide an optical monitoring device and method for sensing optical properties based on measurements made on a single thickness of partially translucent paper sheet material and which measurements sufficiently characterize the actual properties of interest that a minimum of empirical calibration is required regardless of changes in grade and weight of paper.

Another object of the invention is to provide such an optical monitoring device and method capable of accurately sensing optical properties such as brightness, color, opacity and/or fluorescent contribution to brightness.

While such an optical monitoring device is useful off-line for sensing optical properties of a single thickness sample, it is a further important object of the present invention to provide such an optical monitoring device which is of sufficiently light weight and compact construction so as to be adapted for on-line monitoring of the desired optical properties.

Another and further object of the invention is to provide an on-the-paper-machine optical monitoring device of sufficient flexibility and accuracy to enable control of desired optical properties during the paper making process.

A unique feature of the on-line optical monitoring device is its ability to simultaneously measure both reflected and transmitted light. By measuring two independent optical parameters it is possible to thoroughly characterize the paper optical properties of a partially translucent web with a minimum of empirical correction for factors such as paper grade and weight.

Other objects, features and advantages of the present invention will become apparent from the following detailed description taken in connection with the accompanying drawings.

INCORPORATION BY REFERENCE

For a disclosure of an exemplary computer program for use in implementing the present invention, reference is made to FIGS. seven through twenty and the description thereof (beginning at column 28, line 45) of U.S. Pat. No. 4,019,819 issued Apr. 26, 1977.

BRIEF DESCRIPTION OF THE DRAWINGS

FIG. 1 is a fragmentary somewhat diagrammatic longitudinal sectional view of a paper machine showing in outline a side view of an optical monitoring device in accordance with the present invention operatively mounted on line with the machine;

FIG. 2 is a fragmentary somewhat diagrammatic transverse sectional view of the paper machine of FIG. 1 and taken generally as indicated by the line II—II of FIG. 1 and looking in the direction of the arrows (toward the wet end of the paper machine), the view being taken so as to show in outline a direct front view of the optical monitoring device of FIG. 1;

DESCRIPTION OF THE PREFERRED EMBODIMENTS

Figure 3:
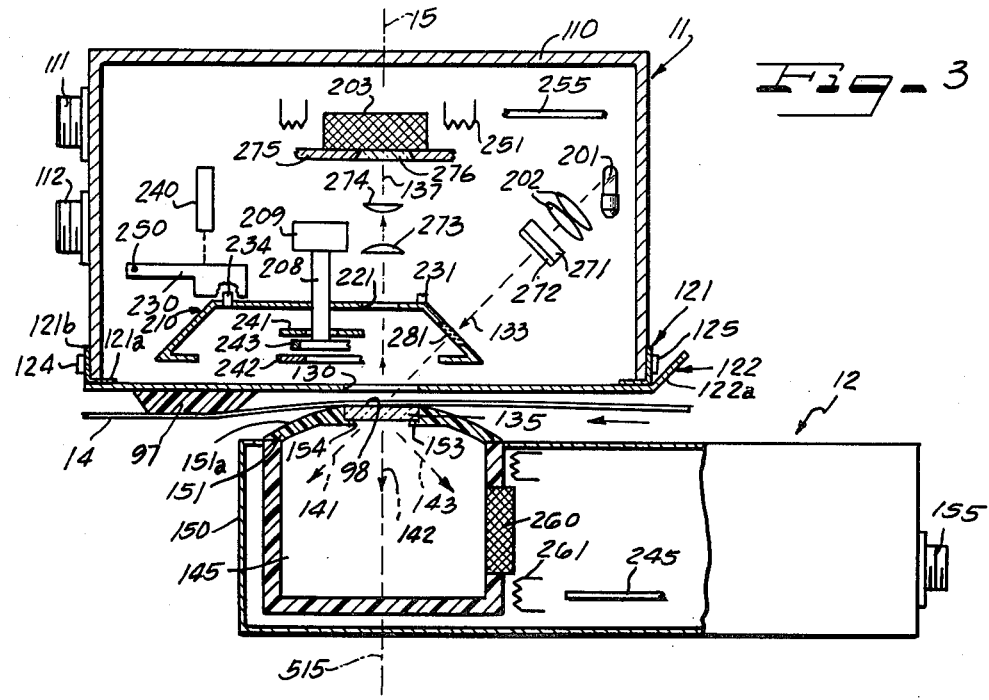
FIG. 3 is a diagrammatic longitudinal sectional view of an on-the-paper-machine optical monitoring device in accordance with the present invention.

Detailed Description Of The Apparatus Of FIGS. 1 and 2

FIGS. 1 and 2 will serve to illustrate the modifications of an existing paper machine which are required for carrying out a preferred embodiment of the present invention. Referring to FIGS. 1 and 2, an on-the-paper-machine optical monitoring device is diagrammatically indicated at 10 and comprises an upper sensing head 11 and a lower sensing head 12 which are maintained in precise relative alignment and disposed for operative association and transverse scanning movement relative to a paper web located as indicated at 14 in FIGS. 1 and 2. As will be described hereinafter with reference to FIGS. 3 and 4, in a particular design of the optical monitoring device, upper head 11 includes a light source for projecting light onto the web such that a portion of the light is reflected parallel to an optical axis indicated at 15, while a further portion of the light is transmitted through the paper web for collection and measurement by means of the lower sensing head 12.

For purposes of illustration, FIGS. 1 and 2 show portions of an existing web scanner construction which is utilized to scan the web 14 for conventional purposes. The conventional scanner construction includes fixed frame components such as 20, 21 and 22 forming what is known as an "O" type scanner frame. The conventional scanning structure further includes upper and lower slides 25 and 26 for joint horizontal movement along the horizontal beams 21 and 22. Associated with the slides 25 and 26 are movable assemblies 27 and 28 carried by the respective slides 25 and 26 and including vertically disposed plates 31 and 32 and angularly disposed flange members such as indicated at 33 and 34 in FIG. 1. These flange portions 33 and 34 have broad surfaces lying in planes generally parallel to the plane of the web 14 and are utilized for mounting of the monitoring device 10 of the present invention. In particular a top head mounting bracket is indicated at 41 in FIGS. 1 and 2 and is shown as being secured to the existing flange part 33 so as to mount the upper head 11 for scanning movement with the assembly 27. Similarly a lower head mounting bracket is indicated at 42 and is shown as being secured to flange part 34 of the lower movable assembly 28 so as to mount the lower sensing head 12 for scanning movement jointly with the upper sensing head 11.

For the purpose of electrical connection with the monitoring device 10 during its traverse of the web 14, electric cables are indicated at 51 and 52 for electrical connection with the components of the upper sensing head 11 and lower sensing head 12 of the monitoring device 10. The cable 51 is shown as being fastened by means of straps 53 and 54 to a top carrier slide bracket 55. The bracket is shown as being secured by means of fasteners 56 and 57 to the upper portion of vertical plate 31. As indicated in FIG. 2, successive loops of cable 51 are secured to swivel type ball bearing carriers such as indicated at 61. A trolley track 62 is supported from existing channels such as indicated at 63 and mounts the carriers 61 for horizontal movement as required to accommodate the scanning movement of the monitoring device 10 across the width of the web 14. Similarly, successive loops of the cable 52 are fastened to the eyes such as indicated at 71 of a lower series of carriers 72. As seen in FIG. 1 each of the carriers such as 72 includes a pair of rollers such as 73 and 74 riding in the trolley track 75 which is secured directly to the lower flange 22a of beam 22. A lower carrier slide bracket 81 is secured to vertical plate 32 by means of fasteners 82 and 83 and is provided with a horizontally extending flange 84 for engaging with the first of the series of lower carriers 72. In particular, carrier 72 is provided with a shank 85 which extends into a longitudinal slot 84a of flange 84. Thus, the first carrier 72 is interengaged with the bracket 81 and is caused to move with the lower assembly 28 and the lower sensing head 12. The remaining lower carriers such as that indicated at 83 move along the trolley track 75 as necessary to accommodate movement of the monitoring device 10 transversely of the web 14.

While FIGS. 1 and 2 have illustrated the optical monitoring device of the present invention as being mounted on line with the paper machine and have further illustrated the case where the monitoring device is to be scanned transversely of the web, it is considered that the optical monitoring device of the present invention would also be of great value if redesigned for bench mounting. By placing a single sheet of paper in a sample mount of the device, a technician could simultaneously test the sample for color, brightness, fluorescence, and opacity in a matter of seconds.

In the illustrated embodiment, however, it is contemplated that the monitoring device 10 will be mounted on line with the paper machine and will be capable of movement to a position clear of the edge of the web as indicated in FIG. 2 at the end of each hour of operation, for example. When the end of a production run for a given web 14 has been reached, or when a web break occurs for any other reason (such as accidental severance of the given web), the monitoring device 10 will be moved clear of the edge of the web path as indicated in FIG. 2. Each time the monitoring device 10 is moved to the off-web position shown in FIG. 2. it is preferred that readings be taken of the reflectance and transmittance values (without the web in the optical path) for the purpose of obtaining an updated calibration of the monitoring device. Thus, such updating of calibration may take place automatically (for example under the control of a process control computer controlling the paper manufacturing operation) at hourly intervals and also after web breaks. The monitoring device can, of course, be retracted manually any time desired by the operator for the purpose of checking calibration. By way of example, the monitoring device 10 may be capable of a normal scanning travel over a distance of 115 inches with provision for an additional travel of 16 inches to the position shown in FIG. 2. A flange is indicated at 87 which serves to insure proper re-engagement of the sensing head with the web at the operator's side of the illustrated paper machine (opposite the side indicated in FIG. 2).

The lower head 12 is designed to contact the web 14 during scanning thereof. The design spacing between the upper and lower heads 11 and 12 is 3/16 inch. The optical opening in the upper head 11 is aligned with the optical axis 15 and is to be maintained in alignment with the center of the window in the lower head 12. Four adjusting screws such as those indicated at 91 and 92 are provided for accurate positioning of the upper head 11. Similarly four position adjusting screws such as 93 and 94 serve for the accurate positioning of the lower head in conjunction with set screws such as indicated at 95 and 96. The adjusting screws are located at each corner of mounting brackets 41 and 42.

Modifications of FIGS. 1 and 2 To Insure Accurate Scanning

Where the web is relatively deeply crowned, it is desirable to provide a web deflecting guide bar as indicated at 97 for insuring stable contact between the web 14 and the web engaging surface 98 of the lower sensing head 12. By way of example the guide bar may protrude from the lower surface of the upper sensing head a distance of 5/16 inch so as to overlap with respect to the vertical direction a distance of ⅛ inch relative to the lower sensing head web contacting surface 98. The guide bar 97 may have a width to force down at least about four inches of the width of the web at a section of web centered with respect to web engaging surface 98 of the lower sensing head relative to the machine direction. This insures a minimum of a ⅛ inch bellying of the sheet as it travels over the lower sensing head in all lateral positions of the sensing head.

In order to minimize changes in the 5/16 inch thickness dimension of the guide bar 97 due to wear, the guide bar is provided with a flat web engaging surface 97a which has a dimension in the direction of web movement of about one inch. By way of example, the guide bar may be made of Teflon.

Since the guide bar 97 is not necessary when the web is fed from the calender stack to the reel in a relatively planar configuration, it has not been shown in FIGS. 1 and 2.

Various modification may of course be made to adapt the monitoring device of the present invention to various types of paper machinery, and to secure any desired degree of accuracy in the joint scanning movement of the upper and lower sensing heads relative to the paper.

Figure 4:
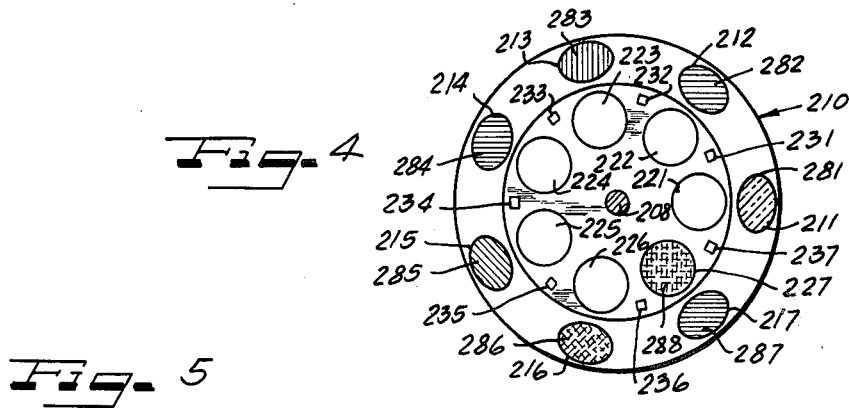
FIG. 4 is a partial diagrammatic plan view of the filter wheel assembly utilized in the monitoring device of FIG. 3.

Structure Of The Optical Monitoring Device As Shown in FIGS. 3 and 4

Referring to FIG. 3, the upper sensing head 11 is shown as comprising a casing 110 having suitable connectors 111 and 112 for receiving suitable internally threaded fittings 114 and 115, FIG. 1, associated with the electric cable 51. The casing 110 receives a top head shoe 120 including an interior open rectangular frame 121 having a base flange 121a spot welded to shoe plate 122. The upstanding portion 121b engages the adjacent wall of casing 110 along all four sides thereof and is secured to the casing 110 by suitable fastening means such as indicated at 124 and 125 in FIG. 3. An edge 122a of shoe plate 122 is bent up at an angle of 45° at the side of the sensing head 11 facing the wet end of the paper machine, and a similar inclined edge 122b, FIG. 1, is provided at each of the sides of the sensing head so as to present smooth faces to the paper web during scanning movement of the sensing head. The shoe plate 122 is provided with a circular aperture of less than one inch diameter as indicated at 130 centered on the optical axis 15 of the device. In a present embodiment aperture 130 has a diameter of about ⅝ inch. This aperture 130 is preferably of minimum diameter necessary to accommodate the light paths of the instrument. In the illustrated embodiment the light path for the incident light beam as indicated at 133 is directed at an angle of approximately 45° and is focused to impinge on a window 135 at the optical axis 15. A reflected light path as indicated at 137 is normal to the web engaging surface 98 (which is the upper surface of window 135), and is coincident with the optical axis 15, while light transmitted through the web 14 and through the window 135 is directed as indicated by rays 141–143, for example, into an integrating cavity 145 of lower head 12.

The lower head 12 comprises a casing 150 having an annular dished plate 151 secured thereto and providing a generally segmental spherical web-contacting surface 151a surrounding window 135. The window 135 is preferably formed by a circular disk of translucent diffusing material. In the illustrated embodiment the window 135 is made of a polycrystalline ceramic material available under the trademark "Lucalux" from the General Electric Company. This material has physical properties similar to that of sapphire. The opposite faces of window 135 are flat and parallel and the thickness dimension is 1/16 inch. A lip is indicated at 153 for underlying an annular edge portion of window 135. This lip provides a circular aperture 154 having a diameter of about 15/16 inch so that the effective viewing area for the transmitted light is determined by the diameter of aperture 154. The casing 150 is shown as being provided with an electrical connector terminal 155 for receiving a suitable internally threaded fitting 156, FIG. 1, of cable 52.

As diagrammatically indicated in FIGS. 3 and 4, the upper sensing head 11 includes a light source 201, incident optical path means including lenses such as indicated at 202 and a photocell 203 for measuring reflected light returning along the reflected light path 137. A filter wheel 210 is shown diagrammatically as being mounted on a shaft 208 for rotation by means of low torque motor indicated at 209. As best seen in FIG. 4, the filter wheel includes an outer series of apertures 211–217 for selective registry with the incident light beam path 133, and includes a series of inner apertures 221–227 for selective registry with the reflective light beam path 137. The various apertures may receive suitable filter elements as will hereinafter be explained in detail such that a series of measurements may be taken by successively indexing the filter wheel 210 to successive operating positions. In each operating position one aperture such as 211 is in alignment with the incident beam path 133 and a second aperture such as indicated at 221 is in alignment with the reflected light beam path 137.

By way of example, the motor 209 may be continuously energized during operation of the monitoring device, and the filter wheel may be retained in a selected angular position by engagement of a ratchet arm 230 with one of a series of cooperating lugs 231–237 arranged generally as indicated in FIG. 4 on the filter wheel 210. A solenoid is indicated at 240 as being mechanically coupled with rachet arm 230 for momentarily lifting the ratchet arm 230 out of engagement with a cooperating lug such as 231 so as to permit the filter wheel to index one position. Immediately upon release of the energization of solenoid 240, the force of gravity returns the ratchet arm 230 to the position shown in FIG. 3 so as to be disposed in the path of the lugs and thus to engage the next lug in succession such as lug 232 as the motor 209 moves the filter wheel 210 into the next operating position.

As will hereafter be explained in greater detail, reed switches are mounted in circles on respective switching boards 241 and 242, FIG. 3, and the filter wheel shaft 208 carries a magnet 243 for actuating a respective pair of the reed switches in each operating position of the filter wheel 210. Thus the position of the filter wheel 210 determines which of the switches on the switching boards 241 and 242 are closed. As will be explained hereinafter, the reed switch on the upper switching board 241 which is closed determines the gain setting of an upper head amplifier at a level appropriate for the set of filters which are in the operating position. The reed switch on the lower switching board 242 which is closed activates a relay on a circuit board 245 in the lower head 12, and such relay in turn sets the lower head amplifier gain at the proper level. As will be explained in connection with the electric circuit diagram for the monitoring device, certain conductors of the cable 51 may be interconnected at a remote location so as to cause an indexing movement of the filter wheel 210. This external command serves to momentarily energize solenoid 240 and lift the ratchet arm 230 about is pivot point 250, allowing the motor 209 to rotate the filter wheel 210. The ratchet arm 230 returns to the position shown in FIG. 3 to catch the next lug on the filter wheel stalling the motor 209.

Four heaters such as indicated at 251 are mounted around photocell 204 so as to minimize the temperature variations of the photocell. A circuit board for mounting an amplifier for photocell 203 and for mounting the gain setting resistances associated with the reed switches is indicated at 255 in FIG. 3.

Referring to the lower head 12, FIG. 3 indicates a photocell 260 for receiving light from the intergrating cavity 145 and a series of heaters such as 261 mounted around the photocell 260 to minimize the temperature variations of the photocell. Circuit board 245 may mount a suitable amplifier for photocell 260, the gain of which being controlled by the relays previously mentioned.

The heaters 251 and 261 in the prototype unit were Pennsylvania Electronics Technology Type 12T55. (These are positive temperature coefficient thermistors with 55° C. switching temperatures.) These heaters will tend to stabilize the temperature since their ability to provide heat decreases as the ambient temperature increases. Above 55° C., they provide essentially no heat at all.

Discussion of Illustrative Operating Details for the Monitoring Device of FIGS. 3 and 4

A basic feature of the illustrated embodiment resides in its ability to measure simultaneously both reflected and transmitted light. While in the illustrated embodiment, the reflected light path 137 and the transmitted light path intersect the web 14 essentially at a common point, reflected light could be obtained from a point on the sample or web offset from the point where light is transmitted through the sample. For example, a backing of some specified reflectance such as a black body of zero or near zero reflectance could be located on the lower sensing head just ahead of or behind the transmitted light receptor compartment (with respect to the machine direction of the sample or the direction of movement of the web). In this case the upper sensing head could contain the light source as well as a reflected light receptor for receiving light reflected from the sample or moving web at a point directly above the backing of specified reflectance. Both the reflected light receptor in the upper sensing head and the transmitted light receptor in the lower sensing head could then supply signals simultaneously and continuously during measurement operations. Many other variations in the arrangement of the optics for measuring both reflected and transmitted light will occur to those skilled in the art.

Referring to the details of the illustrated embodiment, however, and to the case where it is desired to measure brightness, color, opacity and fluorescent contribution to brightness, light source 201, FIG. 3, may consist of a Model 1962 Quartzline lamp operates at 5.8 volts as measured at the lamp terminals. The 45° incident beam path 133 and the normal reflected beam path 137 correspond to those of a standard brightness testor, and a casting (not shown) from a bench type standard brightness tester was used in constructing a prototype of the illustrated embodiment to give rigid support for the optical components such as indicated at 202 and 271-276 in FIG. 3. In the specific prototype unit, a stock thickness polished Corning type 4-69 glass filter 271 and a second type 4-69 filter 272 ground and polished to an appropriate thickness were used in the incident beam path to absorb most of the infrared as well as to give proper spectral response.

The reflected light path 137 includes a pair of lenses 273 and 274 which focus the light on a ⅜-inch aperture in the plate 275 of the casting. A piece of diffusing glass 276 is located on the ⅜-inch aperture so that the light distribution over the surface of photocell 203 will be reasonably uniform. A Weston model 856 RR Photronic cell was employed.

The filter wheel 210 is designed and located in such a way that either the incident or the reflected beam or both can be filtered as desired. In the prototype, the wheel 210 was driven by a small motor 209 operated at reduced voltage so that it could operate continuously in a stalled condition.

Commercially available color and brightness meters are usually manufactured with the spectral response filters located in the reflected beam. In the prototype device, and in the later on-machine version here illustrated as well, however, the filters which determine the spectral response of the first six filter positions are located in the incident beam. There are two basic reasons for this choice of design.

(1) Both the reflected and transmitted light have the same incident intensity and spectral response against which each can be compared. The alternate would necessitate two sets of identical filters, one set located in the reflected beam and another in the transmitted beam—a difficult design to achieve in practice.

(2) Filters in the incident beam can be used to absorb all ultraviolet light and prevent it from striking the specimen. Thus, fluorescence, a phenomenon not accounted for by Kubelka-Munk theory is avoided.

For reasons explained shortly, the seventh filter position is an exception to the above in that substantial ultraviolet light is intentionally permitted to exist within the incident beam. Outside of the phenomenon of fluorescence the spectral response is independent of whether such filters are located in the incident or the reflected beams.

The spectral response provided by the respective positions of the filter wheel 210 were as follows: (1) papermaker's brightness (TAPPI brightness), (2) blue portion of the $E_c\bar{x}$ function, (3) red portion of the $E_c\bar{x}$ function, (4) $E_c\bar{z}$ function without fluorescence (5) $E_c\bar{y}$ function, (6) $E_a\bar{y}$ function, and (7) $E_c\bar{z}$ function, with fluorescence.

As is understood in the art, the symbols $E_c\bar{x}$, $E_c\bar{y}$, $E_a\bar{y}$, and $E_c\bar{z}$ refer to tristimulus functions of wavelength as defined by the Commission Internationale c l'Éclariage which is identified by the abbreviation C.I.E. and is also known as the International Committee on Illumination. The subscript a in the function designation $E_a\bar{y}$ indicates that the function is based on a standardized illumination designated as C.I.E. Illuminant A, while the subscript c in the other function designations refers to a somewhat different standardized illumination which is designated as C.I.E. Illuminant C.

Filters for providing the above spectral response characteristics in the respective operating positions of the filter wheel 210 have been indicated in FIG. 4 by reference numeral 281-288. In the specific example under discussion, apertures 221-226 are left open. Filter 281 is a standard filter for use in measuring TAPPI brightness, TAPPI referring to the Technical Association of the Pulp and Paper Industry. This filter transmits a narrow band of wavelengths in the vicinity of 457 nanometers.

Filters 282–285 are standard filters for a four-filter colorimeter and are conventionally designated X (blue), X (red), Z, and $Y_C$. These filters provide the wavelength distributions required for the measurement of the C.I.E. X, Y, and Z tristimulus values under Illuminant C.

Filter 286 is conventionally designated as a $Y_A$ filter and is required by the TAPPI standard method for opacity measurements. This is a broad band filter producing the C.I.E. Y wavelength distribution for Illuminant A, in conjunction with the source 201 previously described in this section. A discussion bearing on the feasibility of this type of measurement is found in a paper by L. R. Dearth, et al entitled "Study of Instruments for the Measurement of Opacity of Paper, V. Comparison of Printing Opacity Determined with Several Selected Instruments", *Tappi*, volume 53, No. 3 (March, 1970).

With respect to position No. 7 of the filter wheel 210, filters 287 and 288 are conventionally designated as Z (blue) and Z (yellow). As previously indicated, the purpose of the filters is to provide for a determination of the C.I.E. Z tristimulus value with the fluorescence component included. In filter position No. 4, filter 284 serves to remove the ultraviolet component from the incident beam so that a measure of the Z tristimulus value without fluorescence is obtained. In position No. 7 of the filter wheel, however, filter 287 in the incident beam is designed to transmit the ultraviolet component, so that the fluorescent component if any will be transmitted to photocell 203. The ultraviolet absorbing component of the Z type filter means is located in the reflected beam 137, whereas this component is in the incident beam for the No. 4 position. The fluorescent component is lineally related to the difference between the Z tristimulus values determined in the No. 4 and No. 7 positions of the filter wheel 210.

Filters 281–288 have been shown in FIG. 4 with different types of hatching which have been selected to represent generally the different light transmission properties of the filters. In particular, the hatching for filters 281–288 are those for representing white, blue, red, blue, green, orange, blue and yellow light transmission properties. The selection of hatching is primarily for purposes of graphical illustration and is not, of course, an exact representation of the light transmission properties of the respective filters.

Figure 5:
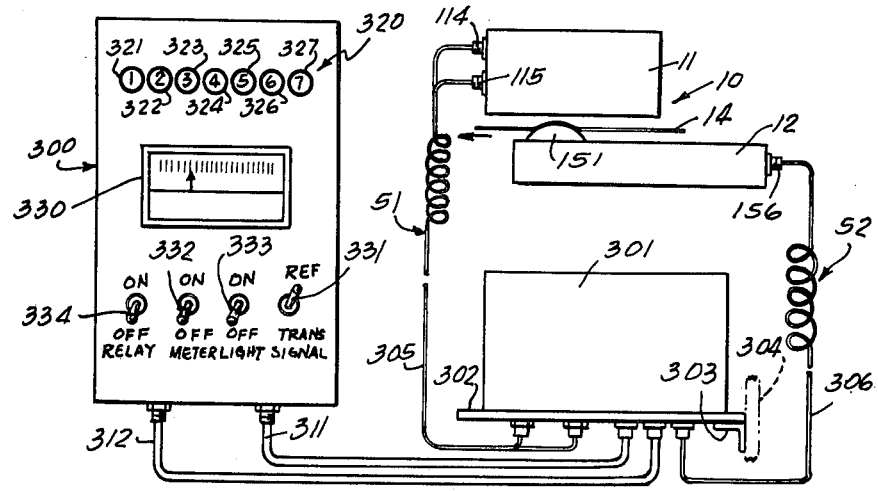
FIG. 5 is a somewhat diagrammatic view illustrating an optical analyzer unit in electrical association with the optical monitoring device of FIGS. 1-4 and with a power supply unit.
Figure 6:
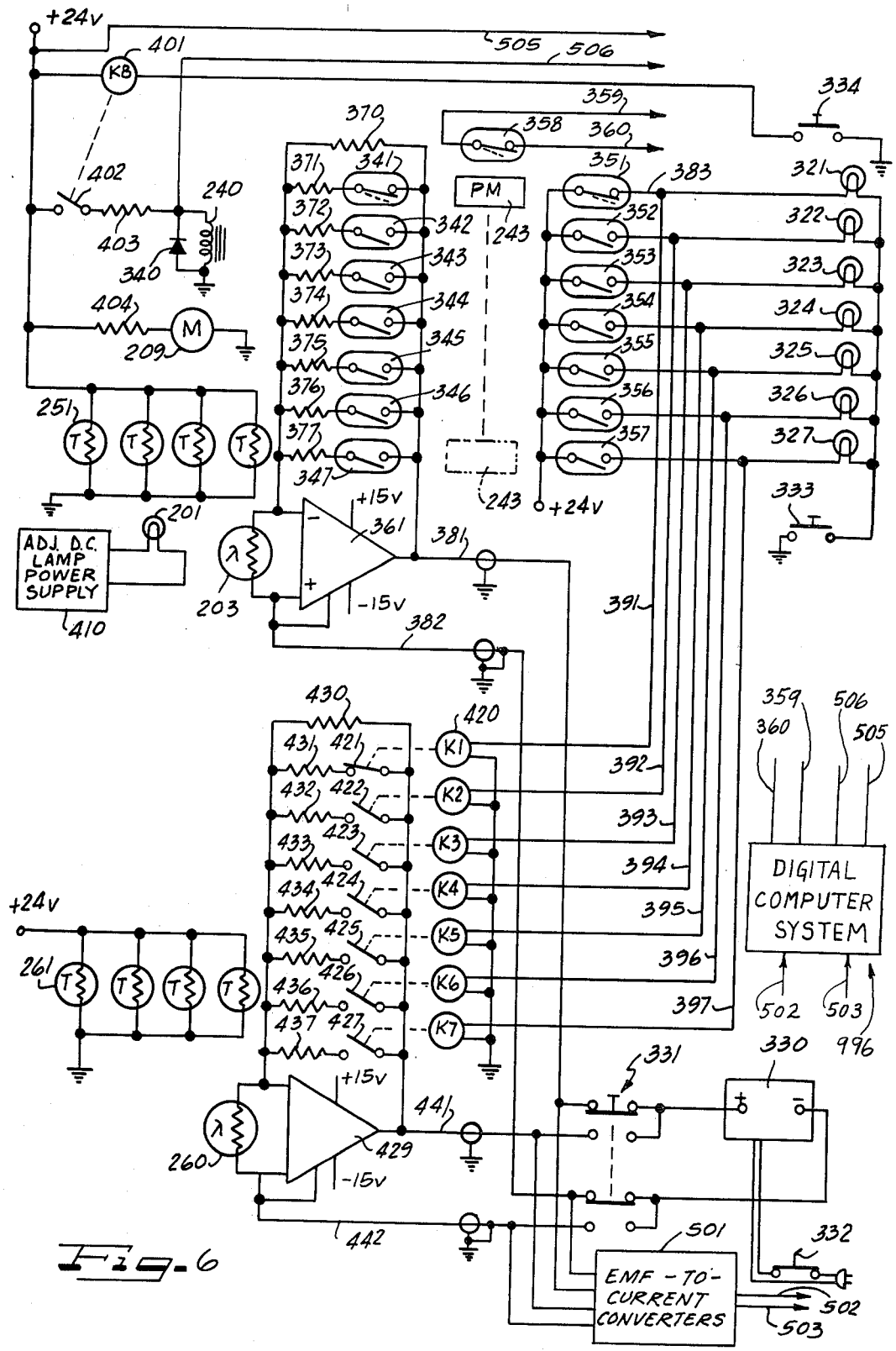
FIG. 6 is an electric circuit diagram illustrating the electrical connections between the various components of FIGS. 1-5.

Detailed Description of FIGS. 5 and 6

FIG. 5 illustrates diagrammatically the optical monitoring device 10 of FIGS. 1–4, and illustrates by way of example an optical analyzer unit 300 which may be electrically associated with the monitoring device and serve as an operator's console to be disposed at a convenient location adjacent the paper machine. By way of example, the optical analyzer unit may be mounted near the dry end of the paper machine, and may receive conventional alternating current power from the paper machine dry end panel. The optical analyzer unit 300 is illustrated as being coupled with the monitoring device 10 via a power supply unit 301 which is mounted adjacent the vertical column 20, FIG. 2, of the "O" frame along which the monitoring device is to travel in scanning the width of the web. For purposes of diagrammatic illustration, power supply unit 301 is shown as being provided with a mounting plate 302 which is secured by means of a bracket 303 to an end of horizontal beam 22 which has been specifically designated by reference numeral 304 in FIGS. 2 and 5. Referring to FIG. 2, it will be observed that the ends 305 and 306 of cables 51 and 52 are adjacent the end 304 of beam 22 so that this is a convenient location for mounting of the power supply 301. The electrical interconnections between the power supply unit 301 and the optical analyzer unit 300 are indicated as extending via a signal conduit 311 and a control conduit 312. By way of example, the signal conduit 311 may contain shielded electric cables for transmitting millivolt signals from the analogue amplifiers of the upper and lower sensing heads 11 and 12. The control conduit 312 may contain conductors which are respectively energized to represent the angular position of filter wheel 210, and may also contain a conductor for controlling the indexing movement of the filter wheel as will be explained in detail in connection with FIG. 6.

Referring to the optical analyzer unit 300 of FIG. 5, the front panel of the unit has been diagrammatically indicated at 320 as being provided with a series of lamps 321–327 for indicating the angular position of the filter wheel 210 within the upper sensing head 11. The lamps 321–327 have been numbered 1 through 7 in correspondence with the seven positions of the filter wheel, and the color of the lamps, for example, may be selected so as to signify the characteristics of the filters located in the openings of the filter wheel such as those indicated at 211–217.

In order to provide a visual indication of the amplitude of the millivolt signals supplied from the sensing heads 11 and 12, a suitable meter is indicated at 330 and a selector switch is indicated at 331 for selectively supplying to the meter the analogue signal from the upper sensing head 11 or from the lower sensing head 12. A switch 332 is indicated for controlling the supply of conventional alternating current power to the meter, and a second switch 333 is indicated for controlling the supply of energizing power for the lamps 321–327. Another switch 334 may be momentarily actuated so as to index the filter wheel 210 to a desired station. The switches 331–334 may, of course, take any desired form, and have merely been indicated diagrammatically in FIG. 5.

Referring to FIG. 6, various of the components previously referred to have been indicated by electrical symbols, and for convenience of correlation of FIG. 6 with FIGS. 1 through 5, the same reference characters have been utilized. In particular, FIG. 6 shows symbolically a light source 201, associated photocells, 203 and 260, filter wheel drive motor 209, control solenoid 240, and permanent magnet 243 which rotates with the filter wheel 210 so as to represent the angular position of the filter wheel. Also shown in FIG. 6, are the four heaters 251 associated with photocell 203, and the four heaters 261 associated with the photocell 260. Further, lamps 321–327, millivoltmeter 330 and switches 331–334 of the optical analyzer unit 300 have been symbolically indicated in FIG. 6.

Referring first to the components associated with the upper sensing head 11, there is illustrated in the upper left part of FIG. 6 a diode 340 connected across solenoid 240. For diagrammatic purposes, permanent magnet 243 is shown arranged between two series of reed switches 341–347 and 351–357. A further reed switch 358 is indicated for actuation in the number 1 position of the filter wheel 210 along with switches 341 and 351. The conductors 359 and 360 associated with switch 358 may be connected with the optical analyzer unit 300, and may be connected via the optical analyzer unit 300 with a remote computer, where the illustrated apparatus forms part of a computer control system for controlling the associated paper machinery.

The reed switches 341-347 are shown as being associated with an operational amplifier 361, so that switches 341-347 serve to select the desired value of feed back resistance for the amplifier in each position of the filter wheel 210. Thus, switches 341-347 served to selectively connect in parallel with resistance 370, additional resistance values 371-377, respectively, for adjusting the total resistance between the input and output terminals of the amplifier 361. Thus, in the number 1 position of the filter wheel, permanent magnet 243 is in a position to actuate switch 341, and connect resistance value 371 in parallel with resistor 370. As will hereinafter be explained, resistance means 371-377 may include variable resistors for adjustment so as to provide the desired gain of amplifier 361 in the respective filter positions, or fixed resistance values may be inserted as indicated, once the desired values have been determined for a given filter wheel. As indicated in FIG. 6, the output of amplifier 361 may be transmitted by means of shielded cables 381 and 382. These cables form part of the overall cable indicated at 51 in FIG. 5 leading from the upper sensing head 11 to the power supply unit 301.

Also forming part of the cable 51 would be the conductors such as indicated at 383 from the respective reed switches 351-357. These conductors such as 383 would connect with respective conductors 391-397 of cable 52 leading from the power supply 301 to the lower sensing head 12.

Included as part of the power supply unit 301 would be components such as relay actuating coil 401, associated normally open contact 402, and resistors 403 and 404 shown at the upper left in FIG. 6. Further, the power supply would include an adjustable direct current lamp power supply component 410 for supplying a precisely adjusted or controlled electrical energization for light source 201. Further, of course, the power supply would supply the required direct current operating potentials for the upper sensing head as indicated in FIG. 6.

The lower left section of FIG. 6 illustrates the electrical conponents of the lower sensing head 12. In the lower sensing head, conductors 391-397 control energization of the operating coils of respective relays K1 through K7. With the permanent magnet 243 in the number 1 position, reed switch 351 is closed, and operating coil 420 of relay K1 is energized closing the associated relay contact 421. The remaining relays K2 through K7 are deenergized, so that the respective associated contacts 422-427 remain open. The contacts 421-427 serve to control the resistance in the feedback path of operational amplifier 429 in conjunction with resistor 430 and resistance means 431-437. As explained in reference to the upper sensing head, resistance means 431-437 may include adjustable resistors, or fixed resistors as shown selected to provide the desired gain of amplifier 429 for the respective positions of the filter wheel 210. The shielded cables 441 and 442 from the output of amplifier 429 connect with power supply unit 301 as part of cable 52. The outputs from the amplifiers 361 and 429 are conducted from the power supply unit 301 to the optical analyzer unit 300 via signal conduit 311, and within the optical analyzer unit connect with respective terminals of the selector switch 331 as indicated at the lower part of FIG. 6. Thus, in the upper position of the selector 331, the output of amplifier 361 is connected with the meter 330, while in the lower position of selector 331, the output of amplifier 429 is supplied to the meter 330. Of course, the optical analyzer 300 may further include analogue to digital converters for converting the outputs of the amplifiers 361 and 429 to digital form for transmission to a remote computer, for example. It will be apparent to those skilled in the art that the remote computer could be programmed to control the sequential actuation of relay 401 during each increment of scanning movement of the monitoring device 10 so as to obtain readings from each desired sampling region of the web 14 for each of the seven positions of the filter wheel 210. The remote computer would then be in a position to correspondingly determine the average optical characteristics of a given length section of the paper web 14, for example, and control suitable inputs to the paper machine so as to maintain desired optical characteristics of the paper being manufactured. Alternatively, of course, the arrangement of FIGS. 1-6 can be utilized simply to take readings from the meter 330 for each filter wheel position during scanning of the web, so as to obtain readings reflecting the optical characteristics of the length sections of the web so scanned. Still further, of course, the circuitry of FIGS. 5 and 6 can be utilized either with the monitoring device located in a fixed position relative to the width of the web (by means of a C-type frame), or with the device off-line from the paper machine, so as to obtain desired readings from the meter 330 for each position of the filter wheel 210 during optical excitation of a single sheet sample of the web held in a sample holder so as to be disposed essentially as indicated for the web 14 in FIG. 3.

Exemplary Commercially Available Components

Commercially available components which are included in the present design of FIGS. 1-6 are as follows.

Main power supply. Lambda Electronics Corporation Model LQS-DA-5124 providing a direct current (DC) output voltage of 24 volts and a maximum current at 40° C. of 5 amperes.

Reed switches. For reflectance amplifier gain settings-Model MMRR-2, and for transmittance amplifier gain settings-Model MINI-2, manufactured by Hamlin, Inc. The relays in the lower sensing head of Type 821A of Grigsby-Barton, Inc.

Operational amplifiers, Model 233J chopper stabilized amplifiers of Analog Devices, Inc. Model 904 power supply supplying plus or minus 15 volts with a minimum full load output current of plus or minus 50 milliamperes.

Digital panel meter (used for off-line studies and for on-line operation before being interfaced with the computer). Weston Model 1290.

Filter wheel advance solenoid Type T 12×13-C-24 volt DC flat plug plunger of Guardian Electric Manufacturing Company, Antibottoming washer made of polyurethane rubber. Operation of the solenoid until interfaced with the computer has been with the use of a time adjusted relay, namely a Model CG 102A6 transistorized repeat cycle timer of G. & W. Eagle Signal Co.

Filter wheel drive motor. Type 1AD3001 Siemens brushless DC motor. The drive belt and pulleys for coupling the motor 209 with the the shaft 208 are specified as positive drive belt FS-80 and positive drive pulleys FC5-20 and FC5-40 of PIC Design Corporation, a Benrus subsidiary. The belt has a stainless steel core and the pulleys have a ¼ inch diameter bore.

Computer Interfacing

In preparing the monitoring device for on-line operation on the paper machine, the zero to 120 millivolt DC signals from the sensing heads will be supplied to respective emf-to-current converters of component 501, FIG. 6. As an example, Rochester Instrument Systems Model SC-1304 emf-to-current converters may be used. Such a converter will provide an output of 10 to 50 milliamperes DC suitable for driving an analog to digital converter at the computer. The emf-to-current converters will provide an isolated input and output so that grounding will not be a problem.

The converters of component 501, will be housed with optical analyzer 300, FIG. 5, and will connect with respective points thirty one of Groups five hundred and six hundred (not shown) at the control computer analog signal input via conductors such as indicated at 502 and 503 in FIG. 6.

Conductors 505 and 506, FIG. 6, associated with filter wheel indexing solenoid 240, FIGS. 3 and 6, may extend within control conduit 312, FIG. 5, and connect with the control computer output terminals at a location designated Group forty two hundred and six, point nineteen (not shown). (Switch 334 should remain open (off) during computer operation of FIGS. 1–6.)

Conductors 359 and 360, FIG. 6, may connect with an input of the control computer at a location designated Group fourteen hundred, point twenty-three (not shown).

DISCUSSION OF AN EARLIER PROTOTYPE SYSTEM

Structure and Operation of a Prototype Optical Monitoring Device

A prototype optical monitoring device was first constructed so as to test the feasibility of the concepts of the present invention. As a result of the experimental work with the prototype system, a preferred system has been designed and will hereinafter be described in greater detail. Since the operation of the prototype system is somewhat different from that of the later designed system, a description of the prototype system will serve to illustrate alternative features and an alternative method of operation in accordance with the present invention.

In the original setting up of the prototype system, the upper and lower sensing heads should be brought into proper alignment and spacing. The spacing should be just under ¼-inch between the case 110 and a surface of the diffusing glass of window 135. (In the prototype unit, there were no additional parts between the case 110 and window 135 such as the shoe plate 122 shown in FIG. 3.) The lower sensing head should be moved laterally in all directions to locate the point where the maximum reading occurs from photocell 260 as well as the point of least sensitivity to relative movement of the upper and lower sensing heads. In an initial calibration of the prototype monitoring device, potentiometers are included as part of the resistance means 371–377 and 431–437 and are adjusted for the respective positions of the filter wheel 210 to give the correct readings for the reflectance and transmittance of the diffusing glass 135 (in the absence any paper sample between the upper and lower sensing heads). The values which were used in this initial calibration are indicative of percentage absolute reflectance and transmittance on a scale of 100, and are as follows:

TABLE 1

Table Showing Exemplary Calibration for the Prototype System- Diffusing Glass Reflectance and Transmittance Values With No Paper Specimen Present

| Filter Wheel Position No. | Reflectance Value, RSD (Millivolts) | Transmittance Value, TSD (Millivolts) |
|---|---|---|
| 1 | 35.4 | 54.0 |
| 2 | 35.0 | 56.1 |
| 3 | 34.4 | 56.9 |
| 4 | 34.6 | 56.6 |
| 5 | 34.7 | 56.4 |
| 6 | 34.5 | 56.6 |
| 7 | 34.8 | 0.6* |

The readings in millivolts can be converted to other desired units by comparing the readings in millivolts for a given paper specimen with the readings obtained with a standard laboratory instrument, measuring the reflectance of the specimen with the laboratory instrument while backing the paper sheet with a piece of Lucalux and a black body. By measuring the reflectance of the single sheet backed with a black body (no fluorescence), the value of transmittance for the specimen can be calculated and this calculated value utilized for calibrating the lower sensing head. If the fluorescent component is included in the laboratory instrument, and if fluorescence is involved, the fluorescence component can be determined by means of a standard reflection meter, and the fluorescent component can then be subtracted from the measured data before making the calculation of transmittance.

The laboratory testing of the prototype system confirmed that a monitoring device such as illustrated in FIGS. 1–4 should have a potential accuracy equal to that of comparable off-line testers provided certain web scanning requirements are met.

Laboratory tests were run on color standard samples of the grades and colors usually run on the paper machine shown in FIGS. 1 and 2. In addition, a variety of opaques, and a variety of colored 50 pound and 70 pound offsets were included in the tests. A four centimeter diameter circle was scribed on each sample to insure that all tests would be done within the same 12 square centimeter section of the sample. Values of $R_o$, $R_\infty$, and TAPPI opacity measurements were made on the available standard laboratory instruments. All test were made on the felt side of the sample with the grain in the standard direction. For $R_\infty$ measurements, the samples were backed by piles of tabs cut from the edge of the same sheet of paper. In addition to the TAPPI opacity measured on the standard opacimeter, TAPPI opacity was calculated via Kubelka-Munk theory from data obtained with a standard automatic color-brightness tester.

The same paper samples were clamped into a holder which held the sample under tension with the lower head of the monitoring device bellying ⅛-inch to ¼-inch into the sheet. The grain of the sheet was oriented parallel to the longitudinal axis of the upper sensing head (that is the machine direction of the sheet was in the same orientation as would occur on the paper machine as indicated in FIGS. 1 and 2). The felt side was always up. Care was taken to make sure that the tested area was within the twelve square centimeter circle scribed on the sample.

The transmittance and reflectance readings were taken from a digital volt meter attached to the output terminals of amplifiers 361 and 429. Calibration data was taken off the Lucalux with no sheet present. Test values were taken on all filters with the sheet in place. The transmittance and reflectance values were keyed into a standard calculator with the calibration data. The calculator was programmed to calculate the color (in C.I.E. X, Y, Z, for example), fluorescent component, brightness, TAPPI opacity and printing opacity (based on $Y_c$). By supplying the basis weight, the computer could also be requested to calculate s, the scattering coefficient (an index of the effect of pigment efficiency and fiber surface area), and k, the absorption coefficient (an index of the effectiveness of dyes in the sheet). The coefficients s and k are especially independent of basis weight. Kubelka-Munk theory is the basis of the calculations used.

All of the samples were tested without changing the relative position of the two sensing heads. One set of data was obtained with the heads in a variety of positions to determine the effect of geometric variations.

Since fluorescence is not compatible with Kubelka-Munk theory, the prototype system was carefully designed so that all data used for Kubelka-Munk analyses have excluded fluorescence. The prototype system measures fluorescence separately. A fluorescent contribution is determined from the prototype data by subtracting the Z distribution reflectance without fluorescence (filter wheel position No. 4) from the Z distribution reflectance with fluorescence (filter wheel position No. 7), and multiplying by the appropriate factor.

As an independent check on fluorescence measurements, a modified brightness tester was utilized which had a filter wheel allowing for standard brightness and Z distribution filters to be put in the reflected beam. In addition, the filter wheel contained brightness and Z distribution filters which had been modified by removing the ultraviolet absorbing component of these fibers. A special mount allows the operator to put the appropriate ultraviolet absorbing filter in the incident beam. Thus, measurements of brightness and C.I.E. Z tristimulus, with and without fluorescence, could be made. Fluorescent contributions were calculated by difference. Some measurements were made on single sheets with a standard backing. Most of the samples were measured with an infinite pack of tabs. The incident beam filter of the prototype's No. 7 position was such that it permitted about twice the standard quantity of ultraviolet light to strike the specimen. Consequently, measurements of the fluorescent contribution measured on the modified brightness tester and the prototype system correlated well (correlation coefficient of 0.992) but the modified brightness tester value is only 0.528 as large as that measured by the prototype system. Calculations of prototype data now involve calculation of the fluorescent component by multiplying the difference of filter positions No. 7 and No. 4 by 0.528.

Because only one fluorescent dye (Tinopal) in all of the paper specimens was used, the fluorescent contribution needed to be measured only once. The prototype data provides a basis for measuring the fluorescent component Z. Measurements by an independent laboratory showed that the paper specimens do not fluoresce significantly in the X (red) or Y distributions; therefore, fluorescent contributions need only be determined for the blue colored distributions. A linear regression was run on the independent laboratory data which demonstrated that the fluorescent component for X (blue) can be predicted by multiplying the fluorescent component for Z by1.204. A regression run on fluorescent data from the modified brightness tester shows that the fluorescent contribution for brightness can be calculated by multiplying the fluorescent contribution for Z by 0.864. In summary, fluorescent contributions are calculated by the following formulas:

$F_Z = 0.528$ (Z reflectance with fluorescence minus Z reflectance without fluorescence.)

$F_{X(blue)} = 1.204\ F_Z$ $F_{Brightness} = 0.864\ F_Z$

These fluorescent contributions are added to the respective calculated $R_\infty$ values when calculating optical properties from prototype data. The test results for fluorescent and non-fluorescent papers agree with values measured on the standard automatic color-brightness tester.

Discussion of the Results of Mechanical Life Testing of the Prototype System and Design Features Selected for the Preferred System in Light of Such Life Testing The following details concerning the results of life testing of the prototype system are considered to reflect minor problems of construction and operation which considered individually are readily corrected for by those skilled in the art. In order to minimize the burden of the total number of such minor problems, and thus to expedite practice of the prototype system, solutions to the various problems which were encountered are briefly referred to.

The filter wheel is advanced by a low torque stallable motor. A timing belt links sprockets on the motor and the filter wheel shaft. The original timing belt had a dacron core. The core of the original belt broke in two places resulting in stretching and eventual loss of teeth. Uneven rate of rotation of the filter wheel occurred due to binding of the belt. Eventually, the plastic drive sprocket broke. Both sprockets were replaced with stainless steel sprockets and the timing belt was replaced with a belt containing a steel core. Installation of the steel sprockets and steel core belt revealed that excessive belt tension could stall the motor. The motor mount holes were slotted allowing the motor to pivot slightly around one mounting screw. Belt tension was adjusted by pivoting the motor. It is concluded that future models should include an idler wheel or some other means of adjusting the tension of the timing belt.

Some problems were experienced with respect to indexing of the filter wheel with the ratchet arm sticking on the tooth so that the ratchet arm does not clear the tooth when a command is give to index the filter wheel. The remedy has been to reduce the roughness of the mating surfaces by filing on the tooth, or smoothing the tooth with a stone. In future models, the shapes and/or smoothness of the ratchet arm and the teeth should be altered to minimize sticking. One solution would be to provide the ratchet arm and the teeth with highly polished mating surfaces.

The ratchet arm is lifted by a 24 volt direct current solenoid. After some time, the plunger of the solenoid became magnetized and would stick to the inside of the coil. This "hanging up" would prevent the ratchet arm from catching the next tooth. A resistor was installed in series with the solenoid coil to reduce the strength of the magnetic field. The plunger of the solenoid was coated with a special material. The coated plunger worked well for about three months before it, too, magnetized enough to hang up. The solution adopted was to provide the solenoid with a flat topped plunger which is stopped at the end of its stroke by a bumper of rubberlike material.

The response of a photocell is somewhat temperature sensitive. For this reasons, it is necessary to keep the photocells at a constant temperature. Ambient temperatures on the O-frame of the No. 6 paper machine indicated in FIGS. 1 and 2 have been measured as high as 118° F. (48° C.) in the summer. The photocells in both heads are mounted in massive metal blocks. Each metal block has four thermistor heaters mounted in close proximity to the photocell. These thermistors have switching temperatures of 55° C., (that is about 130° F.). The intention of this design was to add enough heat to the instrument to hold the temperature steady at about 55° C. During bench studies, this temperature was neve reached due to the low capacity of the heaters. At machine room temperatures, however, the instrument temperature may reach 55° C.

During the bench studies, it was found that the heaters did minimize temperature variations. The few degrees of temperature variation that were observed during normal operation usually occured slowly. Changes in instrument temperature affected the output signal less than acticipated. Based on this experience in the laboratory, the maximum variation in head temperature should be less than 3° F. per hour. Temperature variations of this magnitude will not have a significant effect on the output signal. Long term temperature changes would be corrected for by the calibrations each time the head goes off web.

In the laboratory, there was a minimum of dirt problems. On the machine, however, the hole could allow dirt to enter the upper head. Up to a point, dirt on the lenses and filters will be corrected for by the periodic calibration routine. Excessive dirt, however, will reduce the sensitivity of the instrument and may even affect its accuracy. Periodic cleaning of the lenses and filters will be required. If dirt accumulates too rapidly, it may be necessary to attach an air purge to the upper head.

The lower head of the prototype system is completely sealed so that no dirt problem is anticipated inside the lower head. Because the Lucolux window is in contact with the sheet, friction will keep it clean.

Most of the filters consisted of two or three component parts. There have been some problems with dirt getting between the components of the filters.

The case on the lower head as well as the case on the upper head should allow most general maintenance and trouble-shooting to be done without dismounting the head. A completely removvble case would be desirable. At a minimum access should be provided for the following: (1) convenient light bulb change, (available on the prototype), (2) cleaning of lenses, (available on the prototype), (3) cleaning of the filters. (Access is presently available to one side of each filter. The side which is most likely to collect dirt is not accessible in the prototype.) (4) The amplifier. The amplifier is a standard plug-in module. In the event of a breakdown it could be replaced in seconds if it is accessible. Furthermore, it is necessary to remove the amplifier to do any trouble-shooting on the gain circuitry. (5) The circuit board holding all of the gain control resistors. The choice of gain circuitry is controlled by reed switches which are not accessible on the prototype without a partial disassembly of the instrument. Malfunctions of the reed switches, however, can easily be diagnosed by removing the amplifier and taking resistance measurements on the gain control circuits. There is also the possibility of mechanical or electrical damage to a resistor or a potentiometer mounted on this circit board. With proper access a damaged part could be replaced in five to twenty minutes. (6) The photocell. With proper access, the photocell could be replaced quickly and easily. (7) The heater. The heater are adjacent to the photocell and are generally just as easily serviced. (8) Indexing mechanism. The present accessibility to the ratchet teeth, rachet arm and solenoid is adequate but not very convenient on the prototype. A certain amount of access to these parts is needed to correct chronic indexing problems such as sticking and "hanging up".

The filters are presently mounted in the filter wheel of the prototype by spring clips. Most of the filters are compound filters containing as many as four component pieces of glass. During laboratory trials, increases in the optical density of a filter were frequently observed which could not be corrected by cleaning the surfaces of the filter. Upon removing one of the filters, it was discovered that foreign material was collecting between the components of the compound filter. The use of lens cleaning solution on the filters may have accelerated the problem if capillary action drew foreign material between the components. A set of gaskets and some type of threaded mount should be used to mount the filters in such a way as to minimize foreign material (including cleaning solutions) from getting between the components of compound filters.

In mounting the prototype sensing heads on an O-frame, it is necessary to bring the geometric alignment of the heads as close to their optimum relationship as possible. The original intention was to set the gap between the heads with the aid of a spacer; however, flexibility of the sheet metal case of the prototype upper sensing head prevented the use of a spacer for setting the gap. Accordingly, the shoe plate 122 of the new upper sensing head shown in FIG. 3 has been made of a thickness and consequent rigidity so as to enable the use of a spacer gauge to set the gap between the upper and lower heads. (The gap is reduced by 1/16 inch to 3/16 inch because of the thickness of shoe plate 122.)

The gap between the heads is a most critical dimension as far as calibration and reproducability is concerned. In the prototype it was intended to calibrate relative to an average gap, thus correcting the readings for variations in the gap from the average gap.

One of the criteria used in designing the prototype was minimum head length in the machine direction. Unfortunately, the upper head was turned 90° in order to give the prototype unit the same geometry as the General Electric Brightness Meter, Automatic Color-Brightness Tester, and Hunterlab Color Meter. In this new position, the prototype head is $12\frac{1}{4}$ inches long in the machine direction plus $2\frac{1}{2}$ inches for cable connectors. Redesign should be possible to reduce the machine direction dimension to about 8 inches and to relocate the position of the cable connections.

The lining of the case for the upper head should be matte as well as black to prevent reflection of ambient light within the case and a possible spurious effect on the photocell reading.

Conclusions from Mechanical Testing of the Prototype System

Following the correction of miscellaneous start up problems the prototype system was found to function well mechanically. As a test of its durability, the prototype system was placed in continuous operation for a period of over ten months and no serious mechanical problems resulted except the failure of the solenoid. The solenoid failure was expected and the replacement solenoid is of a design which is expected to give a long service life. The light application of silicone lubricant spray to the indexing control ratchet arm and cooperating teeth corrected a problem of malfunctioning of the filter wheel indexing mechanism (which occurred on two occasions during the ten months). The prototype system was not intended to be a low maintenance instrument; however, the experience during the durability test with the prototype in continuous operation indicates that the prototype system should operate on a paper machine with an acceptably small amount of down time.

DISCUSSION OF LABORATORY TESTING OF FIGS. 3–6

Laboratory Operation of the System of FIGS. 3–6

In the prototype system, potentiometers are included as part of the resistance means 371–377 and 431–437 and are adjusted for the respective positions of the filter wheel 210 to give desired values such as given in the foregoing Table 1. In the preferred system of FIGS. 3–6, these potentiometers for adjusting amplifier gain are omitted and are replaced with fixed resistors 371–377 and 431–437 selected to give scale readings from meter 330 in the respective filter wheel positions which are well above the values given in the preceding Table 1. This is intended to improve the stability and increase the sensitivity of measurement.

In calculating optical parameters from measurements relative to various samples, values were first established for the reflectance RD of the diffuser 135, FIG. 3, in the absence of a paper specimen, for each filter wheel position. Initially calculated values for RD were used in a first computation of optical values, and then the values of RD were adjusted slightly to give the best agreement with the corresponding optical measurements by means of the standard automatic color-brightness tester. The following table shows the reflectance values which were established for certain laboratory testing of the system of FIGS. 3–6.

TABLE 2

Table Showing Reflectance of the Diffusing Glass With No Paper Specimen Present in a Laboratory Test of the System of FIGS. 1–6

| Filter Wheel Position No. | Symbol | Diffusing Glass Reflectance Value |
|---|---|---|
| 1 | RD1 | 0.349 |
| 2 | RD2 | 0.347 |
| 3 | RD3 | 0.355 |
| 4 | RD4 | 0.349 |
| 5 | RD5 | 0.354 |
| 6 | RD6 | 0.354 |
| 7 | RD7 | 0.349 |

The transmittance of the diffusing glass 135 need not be known since the ratio of the transmittance of the diffusing glass and paper (in series) to the transmittance of the diffusing glass is employed in calculating the desired optical parameters.

A computer program was developed to process the data collected during laboratory operation of the monitoring device 10 as well as to compare the calculated reflectance value $R_\infty$ and the calculated fluorescent components with the data collected with the standard automatic color-brightness tester. A listing of the symbols employed in a symbolic statement of the computer program in the Fortran computer language utilized in this laboratory study is set forth in Table 3 on the following pages.

TABLE 3

Listing of Symbols (Including Input Data Symbols and Output Data Symbols With a Brief Indication of Their Significance).

| | Input Data Symbols |
|---|---|
| RSD | OMOD scale reading for reflectance with no paper specimen in place. (Filters 1 through 6.) |
| RSP | OMOD scale reading for reflectance with paper specimen in position. (Filters 1 through 6.) |
| TSD | OMOD scale reading for transmittance with no paper specimen in place. (Filters 1 through 6.) |
| TSP | OMOD scale reading for transmittance with paper specimen in position. (Filters 1 through 6.) |
| RSD7 | OMOD scale reading for reflectance with no specimen in place. (No. 7 filter.) |
| RSP7 | OMOD scale reading for reflectance with paper specimen in position. (No. 7 filter.) |
| $AR_{oo}FC$ | ACBT reflectance including the fluorescent component. |
| AFC | ACBT fluorescent component. |
| RSD4 | OMOD scale reading for reflectance with no paper specimen in place. (No. 4 filter.) |
| RSP4 | OMOD scale reading for reflectance with paper specimen in position. (No. 4 filter.) |
| GC | Grade Correction as determined by the difference between $R_{oo}FC$ and $AR_{oo}FC$ for each sample and each filter. |

| | Output Data Symbols |
|---|---|
| $R_o$ | Reflectance of a single sheet backed with a black body (no fluorescence) as calculated from OMOD data. |
| T | Transmittance of a single sheet backed with a black body (no fluorescence) as calculated from OMOD data. |
| $R_{oo}$ | Reflectance of an opaque pad (no fluorescence) as calculated from OMOD data. |
| $R_{oo}FC$ | Reflectance of an opaque pad (including fluorescence) as calculated from OMOD data. |
| $AR_{oo}FC$ | Reflectance of an opaque pad (including fluorescence) ACBT. |
| DIFF | Difference between $R_{oo}FC$ and $AR_{oo}FC$. |
| FC | Fluorescent component OMOD. |
| AFC | Fluorescent component ACBT. |
| GC | Grade Correction as determined by the difference between $R_{oo}FC$ and $AR_{oo}FC$ for each sample and each filter. |

| | Additional Symbols (Used in the Computation of the Output Data from the Input Data) |
|---|---|
| RK | Reflectance correction factor (assigned a value of 1.000 for laboratory operation). |
| TK | Transmittance correction factor (assigned a value of 1.000 for laboratory operation). |
| RD | Value representing the absolute reflectance of the diffuser (on a scale of zero to 1.000) as adjusted to give best agreement with optical measurements by means of the standard automatic color-bright- |

TABLE 3-continued
Listing of Symbols (Including Input Data Symbols and Output Data Symbols With a Brief Indication of Their Significance).

ness tester. (The values given in Table 2 are used for laboratory operation.)

RPD — Reflectance of paper specimen when backed with the diffuser, as calculated from current values of RK, RD, RSD, and RSP.

TPD — Transmittance of paper specimen and diffuser in series, as calculated from current values of TK, TSD, and TSP.

In the foregoing listing of symbols, the letters of the symbol OMOD are taken from the phrase on-machine otpical device; however, this particular section of the specification refers to a system essentially conforming to the system of FIGS. 3–6 operated to measure optical properties of individual paper sheets under laboratory conditions. (The laboratory work here reported was with an earlier version of the monitoring device designed for on-machine operation, prior to adoption of a thickened shoe plate 122. The standard spacing between the upper and lower sensing heads for the earlier version was ¼ inch, rather than 3/16 inch as with the final version of on-machine device as specifically shown in FIG. 3.) The OMOD scale readings are obtained from the meter 330, FIGS. 5 and 6, with the filter wheel 210, FIGS. 3 and 4, in the respective positions to activate the respective filters 281–286 (indicated as "Filters 1 through 6" in the preceding listing) and to activate filters 287 and 288 (indicated as "No. 7 filter" in the listing), and with switch 331, FIG. 5, in its upper position to measure reflectance, and in its lower position to measure transmittance. As to reflectance measurements, the cavity 145 is considered to form essentially a black body backing for the diffusing glass 135.

The symbol "ACBT" in the foregoing listing of symbols is used to designate a measurement made on the standard commercially available automatic color-brightness tester. The brightness measurement obtained from the ACBT represents a value accepted as standard in the U.S. Paper industry. A further appreciation of the importance of the fact that the OMOD measurements can closely conform to this industry standard is gained from a consideration of the article by L. R. Dearth et al "A Study of Photoelectric Instruments for the Measurement of Color Reflectance, and Transmittance, XVI. Automatic Color-Brightness Tester", *Tappi, The Journal of the Technical Association of the Pulp and Paper Industry*, Vol. 50, No. 2, February 1967, pages 51A through 58A. As explained in this article, the ACBT is photometrically accurate, and the spectral response is correct for the measurement of both color and standard brightness. The spectral response of the ACBT very nearly matches the theoretical CIE functions as indicated by the special technique for determining spectral response. This involves the determination of the tristimulus values for deeply saturated colored glass filters a very rigorous check on the spectral response, especially when it is noted that colored papers are less saturated.

The symbols in the foregoing Listing of Symbols which as shown include lower case characters may also be written exclusively with capital letters. This form of the symbols is convenient for computer printout. The alternate forms of these symbols are as follows: $AR_\infty FC$ or AROOFC; $R_o$ or RO; $R_\infty$ or ROO and $R_\infty FC$ or ROOFC.

TABLE 4
Symbolic Statement of the Computer Program (Used for Processing the Data Obtained During the Laboratory Operation of the System of FIGS. 3-6)

```
6PS FORTRAN D COMPILER
              C OMOD (220)
S.0001          WRITE (6,2001)
S.0002    2001  FORMAT (1H, 'SAMPLE', 6X,
                'RD', 12X, 'T', 12X, 'ROO', 9X,
                'ROOFC', 9X, 1'AROOFC', 10X,
                'DIFF', 7X, 'FC', 7X, 'AFC', 7X,
                'GC',/)
S.0003          READ (5,1000) RK, TK, RD1,
                RD2, RD3, RD4, RD5, RD6
S.0004    102   M = 0
S.0005          READ (5,1000) RSD4, RSP4
S.0006    1000  FORMAT (10F8.0)
S.0007    100   READ (5,1001) IA, IN, ID, RSD,
                RSP, TSD, TSP, RSD7, RSP7,
                AROOFC, AFC, R
S.0008    1001  FORMAT (I2, I2, A4, 9F8, 0)
S.0009          GO TO (11,12,13,14,15,16), IN
S.0010    11    RD = RD1
S.0011          GO TO 17
S.0012    12    RD = RD2
S.0013          GO TO 17
S.0014    13    RD = RD3
S.0015          GO TO 17
S.0016    14    RD = RD4
S.0017          GO TO 17
S.0018    15    RD = RD5
S.0019          GO TO 17
S.0020    16    RD = RD6
S.0021    17    RPD = ((RD*RSP*RK)/RSD)
S.0022          RPD4 = RD4*RSP4*RK/RSD4
S.0023          TPDOTD = (TSP*TK)/TSD
S.0024          RO = (RPD-(RD*(TPDOTD**2)))/(1.-
                (RD* TPDOTC)**2)
S.0025          T = (TPDOTD*(1.-(RD*RPD)))/(1.-
                (RD*TPDOTD)**2)
S.0026          A = ((1.+(RO**2))-(T**2))/RO
S.0027          ROO = (A/2.)-SQR[(((A/2.)**2)-1.)]
S.0028          RPD7 = RD4 *RSP7*RK/RSD7
S.0029          IF (IN-2)1,2,3
S.0030    3     GO TO (7,7,7,4,7,7), IN
S.0031    1     FC = (RPD7-RPD4)*.450
S.0032          GO TO 6
S.0033    2     FC = (RPD7-RPD4)*.570
S.0034          GO TO 6
S.0035    4     FC = (RPD7-RPD4)*.510
S.0036    6     ROOFC = ROO + FC
S.0037          GO TO 30
S.0038    7     ROOFC = ROO
S.0039          FC = 0.0
S.0040    30    IF (IA-2)18,19,19
S.0041    18    ROOFC = ROOFC + R
S.0042          GO TO 20
S.0043    19    ROOFC = ROOFC-1
S.0044    20    DIFF = ROOFC-AROOFC
S.0045          GO TO (21,22), IA
S.0046    21    WRITE (6,2000)ID,RO,T,ROO,
                ROOFC, AROOFC,DIFF,FC,AFC,R
S.0047    2000  FORMAT (IH A4,7X,2(F8.6,4X),4
                (F10.6,4X),2(F5.4,X),'+', F4.3)
                TO TO 23
S.0048
S.0049    22    WRITE (6,2002)ID,RO,T,ROO,
                ROOFC,AROOFC,DIFF,FC,AFC,R
S.0050    2002  FORMAT (1H,A47X,2(F8.6,4X),4
                (F10.6,4X),2(F5.4,4X),'-', F4.3
S.0051    23    M = M + 1
S.0052          IF (M-6) 100,102,102
S.0053          END
                SIZE OF COMMON OOOOO
                PROGRAM O1930
END OF COMPILATION MAIN
```

In the foregoing Table 4, the symbols representing basic mathematical operations were as follows:

| Operation | Symbol | Example |
|---|---|---|
| Addition | + | A+B |
| Subtraction | − | A−B |
| Multiplication | * | A*B |
| Division | / | A/B |
| Exponentiation | ** | A**B($A^B$) |
| Equality | = | A=B |

To indicate more concretely the calculations which are performed, the following Table 5 will illustrate exemplary input and output data for a given sample. The meaning of the various symbols will be apparent from the listing of the symbols of Table 3:

TABLE 5

Table Showing Exemplary Input and Output Data for a Given Sample
Sample No. 1, white Nekoosa Offset-60 pound paper, specimen A RK = 1.000, TK = 1.000

| Filter Wheel Position No. Input Data | 1 | 2 | 3 | 4 | 5 | 6 |
|---|---|---|---|---|---|---|
| RD | 0.349 | 0.347 | 0.355 | 0.349 | 0.354 | 0.354 |
| RSD | 0.515 | 0.529 | 0.583 | 0.636 | 0.525 | 0.596 |
| RSP | 1.161 | 1.187 | 1.339 | 1.422 | 1.191 | 1.357 |
| TSD | 1.422 | 1.625 | 1.627 | 1.702 | 1.625 | 1.546 |
| TSP | 0.236 | 0.256 | 0.354 | 0.277 | 0.335 | 0.326 |
| RSD7 | 0.568 | 0.568 | 0.568 | 0.568 | 0.568 | 0.568 |
| RSP7 | 1.381 | 1.381 | 1.381 | 1.381 | 1.381 | 1.381 |
| AROOFC | 0.837 | 0.829 | 0.847 | 0.830 | 0.839 | 0.844 |
| AFC | 0.034 | 0.034 | 0.0 | 0.036 | 0.0 | 0.0 |
| RSD4 | 0.636 | 0.636 | 0.636 | 0.636 | 0.636 | 0.636 |
| RSP4 | 1.422 | 1.422 | 1.422 | 1.422 | 1.422 | 1.422 |
| GC | −0.006 | −0.014 | −0.021 | −0.007 | −0.009 | −0.012 |
| RO | 0.779777 | 0.772313 | 0.803330 | 0.773563 | 0.792249 | 0.794690 |
| T | 0.120798 | 0.115319 | 0.155529 | 0.118812 | 0.148337 | 0.151546 |
| ROO | 0.812093 | 0.800173 | 0.874419 | 0.803542 | 0.849399 | 0.856230 |
| ROOFC | 0.836794 | 0.824838 | 0.853419 | 0.831337 | 0.840399 | 0.844230 |
| AROOFC | 0.837000 | 0.829000 | 0.847000 | 0.830000 | 0.839000 | 0.844000 |
| DIFF | −0.000206 | −0.004162 | 0.006419 | 0.001337 | 0.001399 | 0.000230 |
| FC | .0307 | .0387 | .0 | .0348 | .0 | .0 |
| AFC | .0340 | .0340 | .0 | .0360 | .0 | .0 |
| GC | −.006 | −.014 | −.021 | −.007 | −.009 | −.012 |

In the foregoing table showing exemplary input and output data, the input and output data symbols have been shown as they are actually printed out by the computer with all letters capitalized. In the text, certain of the input and output data symbols are shown in a more conventional manner with subscripts since the symbols are more familiar in such form.

The data such as exemplified in Table 5 are based on a single determination for each specimen. The "grade correction" GC is based on the average difference between $R_\infty FC$ and $AR_\infty FC$ for two specimens, specimens A and B.

The data as exemplified in Table 5 show that there is generally good agreement between the calculated $R_\infty FC$ and $AR_\infty FC$ values. The spread in values for the duplicate specimens (A and B) is good with the exception of several samples. Some difficulty was experienced in positioning the specimen on the monitoring device 10 to give reproducible results. The difficulty should be minimized when the unit is placed "on-machine". The grade correction GC takes this discrepancy into consideration so the correction should be established "on-machine".

The RD values shown in Table 5 were punched into the first data card along with the values for RK and TK for input to the computer in advance of a desired computation. The factors RK and TK were included as factors in the computations so that the transmittance and reflectance values could be adjusted independently, if desired. In this evaluation, RK and TK were left at 1.000. (Calculated values for RD were used in a first computer run and then the values were adjusted slightly to give the best agreement with the standard automatic color-brightness tester. The values for RD shown in Table 5 are the slightly adjusted values utilized in obtaining the data discussed in this section of the specification.)

A second set of data from the same fourteen samples was collected using the monitoring device in the same condition as for the collection of the data previously given. All of the variables were left the same to see how closely the data could be reproduced for the identical specimens. The agreement was quite good except for samples 8 and 14. It appears that the paper may not have been lying flat in one or the other tests. The grade correction GC on some of the grades was changed and the second set of data was again calculated for samples 1, 2, 4, 5, 6, 8 and 14. This improved the agreement between the monitoring device and the standard automatic color-brightness tester.

The reflectance head of the monitoring device was then lowered 0.025 inch and another set of data was collected for the same seven samples. The same ACBT data was used. The data show that lowering the reflectance head reduces the reflectance while transmittance remains essentially unchanged. The effects are not as large as was expected and could be corrected through adjustment of RK; however, the variables RK, TK and GC were again held constant.

The reflectance head was then raised to a spacing of 0.050 inch (0.025 inch above the normal position for these tests), and another set of data was collected for the same seven samples. The effects were larger than when the reflectance head 11 was lowered. Again, an adjustment of RK would improve the agreement.

It was concluded from these test results that a change of plus or minus 0.025 inch from "normal position" is larger than can be tolerated. An estimate of a reasonable tolerance, based on this and earlier work, would be plus or minus 0.010 inch from "normal position".

All of the variables used in calculating the data for samples 1, 2, 4, 5, 6, 8 and 14, after the initial change in the grade correction GC, were held the same to determine the effects of changing the reflectance head position. The same input data for the case of the reflectance head being raised 0.025 inch were processed again but with RK equal to 0.975 instead of 1.000. This reduces the reflectance value to the proper level. The data obtained in this way show good agreement between the monitoring device and the standard automatic color-brightness tester. Apparently the factor RK can be used quite effectively in adjusting for some variation in the geometric relationship of the upper and lower sensing heads. It would be preferred, of course, to maintain proper alignment and spacing.

A second set of samples were evaluated after returning the reflectance head to its normal spacing from the transmittance head. Before calculating new output data, the computer program of Table 4 was corrected in statements S.0022 and S.0028 by changing RD to RD4. The corrected computer program has been shown herein since the error in the previously referred to data was insignificant in most cases. Thus with the corrected computer program, the input data for the second set of samples were processed. The values RK and TK were set to 1.000 and the same grade corrections were used as for samples 1, 2, 4, 5, 6, 8 and 14 previously referred to.

Conclusions drawn from all of the data are that the grade correction GC will handle errors resulting from less than ideal characteristics of the monitoring device 10 such as the relatively wide bandwidth of light transmitted in the various filter positions in comparison to the requirements of Kubelka-Munk theory and the fact that this theory applies strictly only to diffuse light rather than collimated light as actually employed in the illustrated monitoring device 10. This correction must be established "on-machine". Use of the diffusing glass 135 to calibrate the monitoring device 10 will handle changes in light level, photocell sensitivity and amplifier gain. The reflectances RD of the diffusing glass 135 for the various filters as established in the present work are set forth in the previous Table 2 entitled "Table Showing Reflectance of the Diffusing Glass With No Paper Specimen Present in a Laboratory Test of the System of FIGS. 1-6".

As previously mentioned, the transmittance of the diffusing glass 135 need not be known as the ratio of the transmittance of the diffusing glass and paper (in series), identified by the symbol TSP, to the transmittance of the diffusing glass 135, identified by the symbol TSD, is employed as will be apparent from the explanation of the calculations employed set forth hereinafter.

The fluorescent component is handled through the difference in reflectance as measured with the number 4 and the number 7 filters (RPD7 minus RPD4). The factors used in the subject computations, for filters number 1, 2 and 4, are 0.500, 0.600 and 0.550 respectively. This means of determining the fluorescent contribution FC appears to be successful.

The factor RK whereby the reflectance can be adjusted to account for misalignment or incorrect spacing seems to function better than was expected.

The following examples will serve to explain the calculations of the output data for the different filter positions in greater detail.

TABLE 6

Table Showing
Exemplary Calculation of Paper
Optical Parameters

Calculation of $R_o, T, R_{oo}, FC$ and $R_{oo}FC$ from OMOD data with the No. 1 filter in position.
Input: RSD1, RSP1, TSD1, TSP1, RSD7, RSP7, TK, RK, RSD4, RSP4, RD1, RD4, and GC1
Calculation:
RPD1 = (RD1 × RSP1 × RK)/RSD1
RPD4 = (RD4 × RSP4 × RK)/RSD4
RPD7 = (RD4 × RSP7 × RK)/RSD7
TPD/TD = (TSP1 × TK)/TSD1
$R_o$ = [RPD1 − (RD1(TPD/TD)$^2$)]/[1 − (RD1(TPD/TD)$^2$)]
T = [(TPD/TD)(1 − (RD1 × RPD1))]/[1 − (RD1(TPD/TD)$^2$)]
A = (1 + $R_o^2$ − T$^2$)/$R_o$ $R_{oo}$ = (A/2) − $\sqrt{(A/2)^2 - 1}$
FC = 0.500 (RPD7 − RPD4)
$R_{oo}FC = R_{oo} + FC + GC1$ Calculation of $R_o, T, R_{oo}, FC$ and $R_{oo}FC$ from OMOD data with the No. 2 filter in position
Input: RSD2, RSP2, TSD2, TSP2, RSD7, RSP7, TK, RK, RSD4, RSP4, RD2 and GC2.
Calculation:
RPD2 = (RD2 × RSP2 × RK)/RSD2
RPD4 = (RD4 × RSP4 × RK)/RSD4
RPD7 = (RD4 × RSP7 × RK)/RSD7
TPD/TD = (TSP2 × TK)/TSD2
$R_o$ = [RPD2 − (RD2(TPD/TD)$^2$)]/[1 − (RD2(TPD/TD)$^2$)]
T = [(TPD/TD)(1 − (RD2 × RPD2))]/[1 − (RD2(TPD/TD)$^2$)]
A = (1 + $R_o^2$ − T$^2$)/$R_o$ $R_{oo}$ = (A/2) − $\sqrt{(A/2)^2 - 1}$
FC = 0.600(RPD7 − RPD4)
$R_{oo}FC = R_{oo} + FC + GC2$ Calculation of $R_o, T, R_{oo}, FC$ and $R_{oo}FC$ from OMOD data with the No. 3 filter in position
Input: RSD3, RSP3, TSD3, TSP3, TK, RK, RD3 and GC3
Calculation:
RPD3 = (RD3 × RSP3 × RK)/RSD3
TPD/TD = (TSP3 × TK)/TSD3
$R_o$ = [RPD3 − (RD3(TPD/TD)$^2$)]/[1 − (RD3(TPD/TD)$^2$)]
T = [(TPD/TD)(1 − (RD3 × RPD3))]/[1 − (RD3(TPD/TD)$^2$)]
A = (1 + $R_o^2$ − T$^2$)/$R_o$ $R_{oo}$ = (A/2) − $\sqrt{(A/2)^2 - 1}$
FC = 0.0
$R_{oo}FC = R_{oo} + FC + GC3$ Note: The calculations for Filters No. 5 and 6 are carried out in the same manner as for filter No. 3 except that the appropriate filter data are employed. FC is made equal to zero for filters No. 3, 5 and 6 for all samples.

Calculation of $R_o, T, R_{oo}, FC$ and $R_{oo}FC$ from OMOD data with the No. 4 filter in position.
Input: RSD4, RSP4, TSD4, TSP4, RSD7, TK, RK, RD4 and GC4.
Calculation:
RPD4 = (RD4 × RSP4 × RK)/RSD4
RPD7 = (RD4 × RSP7 × RK)/RSD7
TPD/TD = (TSP4 × TK)/TSD4
$R_o$ = [RPD4 − (RD4(TPD/TD)$^2$)]/[1 − (RD4(TPD/TD)$^2$)]
T = [(TPD/TD)(1 − (RD4 × RPD4))]/[1 − (RD4(TPD/TD)$^2$)]
A = (1 + $R_o^2$ − T$^2$)/$R_o$ $R_{oo}$ = (A/2) − $\sqrt{(A/2)^2 - 1}$
FC = 0.550(RPD7 − RPD4)
$R_{oo}FC = R_{oo} + FC + GC4$ On the basis of further experimental data, the factors relating the fluorescent component, as measured on the monitoring device, to the fluorescent component as measured with the standard automatic color-brightness tester, have the following presently preferred values for filter wheel position numbers 1, 2 and 4: 0.528, 0.636, and 0.456, respectively.

DISCUSSION OF THE ON-MACHINE SYSTEM OF FIGS. 1–6

Set Up Procedure For the System of FIGS. 1–6

In the prototype system, potentiometers were included as part of the gain control resistance means and were adjusted for the respective positions of the filter wheel 210 to give values correlated directly with absolute reflectance and transmittance of the diffusing glass, such as given in the foregoing Table 1. In the preferred system of FIGS. 1–6, however, these potentiometers for adjusting amplifier gain are omitted and are replaced with fixed resistors 371–377 and 431–437 selected to give scale readings from meter 330 in the respective filter wheel positions which are well above the values given in Table 1. The higher gain values selected for the amplifiers 361 and 429 in the preferred system are intended to provide improved stability and increased sensitivity of measurement.

The upper and lower sensing heads are placed at a spacing of 3/16 inch by means of a gauging plate made of 3/16 inch Teflon. The incident beam 133 forms a light spot of elliptical configuration on the planar upper and surface 98 of the diffusing window 135. The major axis of the elliptical light spot has a length of about ⅝ inch and is parallel to the direction of web movement, i.e. the machine direction, while the minor axis has a length of about ⅜ inch and is at right angles to the machine direction. The reflected beam 137 consists of the total light reflected from a circular spot of approximately ⅜ inch diameter. This viewed area lies substantially within the elliptical illuminated area on surface 98; however, the two essentially coincide in the direction of the minor axis of the illuminated spot.

Since the effective optical aperture 154, FIG. 3, of the lower sensing head is of a diameter of about 15/16 inch, the system will be insensitive to a certain amount of lateral offset between the optical axis 15 of the upper sensing head and the optical axis 515 of the lower sensing head.

In setting up the system, the position of the lower sensing head may be adjusted laterally so that the spot formed by the incident beam 133 is essentially centered on the surface 98 of window 135.

The optimum relationship between the upper and lower sensing heads can be precisely detected by observing the reflectance output from the upper sensing head (in any position of the filter wheel 210) as the heads are moved relative to one another while maintaining the spacing of 3/16 inch between the heads. When the correct geometrical relationship is attained between the incident beam 133, the reflected beam path 137 and the plane of the surface 98 of the window 135, the reflectance signal will have a maximum value.

With the upper and lower sensing heads in the optimum geometric relationship, and with the incident beam impinging on the central part of surface 98, it is considered that relative shifting between the upper and lower heads in the plane of surface 98 over a range of plus or minus ⅛ inch in any lateral direction should have an insignificant effect because of the flat planar configuration of surface 98.

Discussion of the Present Disclosure

A basic conception of the present disclosure is crucially concerned with the art of paper manufacture wherein numerous grades and weights of paper are to be manufactured, and wherein access to the paper web for measurement of paper optical properties during the manufacturing process is restricted to a section between the calendering stack and the reel. By measuring two essentially independent optical parameters, for example measuring both the reflectance and transmittance with respect to incident light of the necessary spectral distribution, it is possible to calculate paper optical properties on the basis of existing theory with an essential independence of basis weight.

Closely related to the foregoing is the conception of utilizing as nearly as practicable the optical response characteristics and geometry of existing instruments used in the paper industry, so as to achieve as close a correlation as possible with present off-line measurements of color and brightness, for example. Also of substantial significance is the conception of providing a rugged and compact temperature-stabilized instrument capable of reliable and accurate on-machine measurement of color, brightness and opacity.

An important aspect of the disclosure relates to the simultaneous measurement of the basis weight of the moving paper web, such that paper optical response parameters such as the scattering coefficient S and the absorption coefficient K are obtained with essential independence of any variations in the basis weight of the paper sheet material at successive scanned regions along the length of the web.

The term on-machine optical monitoring device is intended generically and refers to the device 10, FIGS. 1 and 2, and other comparable devices for sensing two essentially independent optical response parameters such that a paper optical property is characterized prior to use of any correction factors with substantially improved accuracy in comparison to any characterization (prior to correction factors) of such paper optical property from either of such optical response parameters taken by itself. Such a monitoring device may be used as an aid to manual control of the paper making process or may be used as part of a closed loop automatic control system. Thus "monitoring" does not exclude active control in response to the output signals from the monitoring device.

Within the scope of the present subject matter, one or more of the following paper optical properties may be sensed: brightness, color, fluorescence, and/or opacity. Control of brightness and fluorescence offers a very substantial potential for cost reduction in the production of a significant range of paper types. Color control, on the other hand, may have important consequences regarding flexibility of manufacture, product uniformity, and grade change flexibility.

The value of on-line opacity control has already been demonstrated to a large degree in a prior closed loop analog opacity controller. In this installation, the average opacity across the web is controlled almost exactly at any given desired value. In previous manually controlled operations, the PKT (Pigmentary Potassium Titanate $K_2O-6T_iO_2$ by du Pont) flow was set to some value chosen by the beater engineer and usually held to such value for the duration of the run of a given grade and weight. In the meantime, the paper opacity varied up and down, depending on process conditions at the time. Since the installation of the analog opacity controller, the opacity set point is adjusted rather than the PKT flow, thus holding opacity constant at the desired level. Instead of opacity, the PKT flow now varies up and down to compensate for other presently unavoidable process upsets resulting from variations in broke richness, PKT solids, dye usage, save-all efficiency, and other machine retention conditions. For a complete discussion of the installation of the analog opacity controller, reference is made to F. P. Lodzinski article "Experience With a Transmittance-Type On-Line Opacimeter for Monitoring and Controlling Opacity", *Tappi*, The Journal of The Technical Association of The Pulp and Paper Industry, Vol. 56, No. 2, February 1973. This article of February, 1973 is incorporated herein by reference.

Existing on-line color meters have two serious disadvantages as follows:

1. Each measures a reflectance value ($R_g$) which is decidedly different from that necessary for actual color and brightness characterizations. Off-line instruments, which adequately measure these properties, require that a pad of several thicknesses ($R\infty$) of the same paper be exposed to the light source aperture. Obviously, this is impossible with an on-line instrument, unless the far more inaccessible reel itself is tested. The use of $R_g$ instead of $R\infty$ requires very frequent off-line testing, and constant updating of an empirical calibration procedure to maintain adequate accuracy. A separate set of calibration parameters for each grade and weight is also required. Only in instances of extremely high opacity such as heavily coated, or heavily dyed colors where $R_g$ approaches $R\infty$, can the above problems be minimized to the point where accuracy becomes sufficient for control purposes.

2. Existing color instruments are not equipped to measure transmitted light which is much more sensitive to differences and, so far, the only commercially proven method for the continuous monitoring of opacity.

To assist in indicating the scope of the present disclosure, the substance of excerpts from an early conception record with respect to the present subject matter are set forth in the following paragraphs, headed "Proposal" and "Proposed Instrument Design" having reference to the defects of existing on-line color meters just discussed:

Proposal

An instrument built to the general specifications disclosed in the following section headed "Proposed Instrument Design" avoids the above described defects and, at the same time, provides for a concise, but extremely versatile, nearly total optical property monitor and controller. Highly trained specialists in all fields required here, including paper optics, color theory, photometry, computers, and others, if needed are available. As an example, exact specifications for the filters, photocells, and light sources are essentially ready for manufacture now. Such specialists are also aware of factors important to optical characterization frequently ignored by commercial producers of optical instruments.

Proposed Instrument Design

An instrument made up of two scanning sensing heads, one above and one below the moving paper web, and a dedicated computer with appropriate couplers for input and output, is envisioned. The bottom head would receive light transmitted through the sheet and subsequently analyzed for its X, Y, and Z tristimulus components. It would also contain a backing of some specified effective reflectance (possibly a black body of zero, or near zero, reflectance) located just ahead or behind (machine direction) of the transmitted light receptor compartments(s).

The upper head could contain the light source, as well as a reflected light receptor. The latter occurs after reflection from the moving web at a point just above the backing, on the bottom head and would also be analyzed for its X, Y, and Z tristimulus components. Both light receivers and, for that matter, the light source itself could be integrating cavities of a type. This would be one way to insure the uniform distribution of emitted, transmitted, and reflected light in the X-direction in addition to providing identical samples of light going to each photoelectric cell installed with filters within the cavities themselves. Thermostatically controlled heaters or coolers would likely be desirable for temperature control. The flux of the light source could be monitored or controlled by a third partial, or full, set of filter-photocell combinations. The availability of both the transmitted (T) and reflected ($R_g$) light signals described above allows for precise computation of the reflectance with an infinite backing ($R\infty$). It is the latter, $R\infty$ value, which is required to characterize color, brightness, and an index of fluorescence. In addition, it would eliminate the need for any grade corrections in measuring either printing or TAPPI opacity, both of which could be made available if desired.

A small, rather low-cost, dedicated computer with appropriate interface equipment, could be used to receive all signals, compute all pertinent optical properties, and determine the signal for direct, closed loop control of:

a. 2–5 separate conventional dye additions;
b. fluorescent dye feed to the size press; and
c. PKT, $TiO_2$, or other slurry flow;

so that brightness, opacity, color (L, a,b) and fluorescence could be maintained almost exactly as chosen by, perhaps even a master computer, if desired.

Kubelka-Munk equations, quantitative color descriptions, and their inter-relationships, recently acquired wet end mathematical models, along with existing control theory, are all presently available in some form or other to convert the input signals from the scanning heads to optical measurements and flow feeds with which paper manufacturers are familiar. The combined mathematical technology above is also sufficient for adequate decoupling of this otherwise complicated information so that overlapped control is avoided.

Use of a dedicated computer would eliminate most of the electronics now associated with optical measuring equipment. It could also be used to integrate results across the web and simplify and/or maintain calibration. The package would lend itself to rather universal application and minimize the time and effort on the part of the purchaser.

The key feature of this proposed instrument, which distinguishes it from existing on-line optical testers, is that it calls for the measurement of both transmitted and reflected light without undue complications. This, in turn, can cause a great deal of improvements regarding sensitivity, accuracy, flexibility, and thoroughness of a continuous optical property measuring device.

Scope of the Early Conception of This Invention

Given the foregoing conception, it is considered that many modifications and variations will be apparent to those skilled in the art. The basic conception claimed herein is the sensing of two essentially independent optical response parameters of a single thickness relatively homogeneous sheet material such that any other desired parameter or paper optical property can be accurately calculated.

The present subject matter is limited to the determination of the specified optical properties of single thickness relatively homogeneous sheet material with the use of filters of the appropriate spectral response characteristics as explained in the present specification. For the case of opacity measurement, for example, the present invention, is particularly applicable to an optical system wherein system spectral response essentially simulates the C.I.E. tristimulus Y filter with either illuminant A or C and to near-white papers as explained in the Lodzinski Article of February, 1973 incorporated herein by reference.

PROPOSED OPTICAL CONTROL STRATEGY

While the on-line automatic control of paper optical properties is an ultimate objective of the work reported herein, the claimed subject matter relates to on-machine monitoring of paper optical properties whether used as an aid to conventional manual control or for other purposes. Nevertheless, in order to provide a disclosure of the best mode presently contemplated for automatic control as a separate but related area of endeavor, the following discussion is presented.

The optical properties of a sheet of paper are dependent upon all of the materials of which it is made but primarily upon the furnished pulp, fillers, pigments, dyes, and some additives. It is often very difficult to maintain the optical attributes of the pulp, fillers and additives constant within a given production run. Such variation is even greater between runs. The optical properties of the finished paper may, however, be reasonably controlled to specified standards by varying the additions of dyes and fillers and pigments until the desired compensations are achieved. The problem is that each furnished ingredient affects each of the resulting paper optical properties in a rather complicated manner. Indeed the intuition of experienced papermakers has essentially been the sole method of optical property control. Unfortunately, this approach is inefficient, resulting in considerable off-standard paper and/or waste of costly materials. Accordingly, a dire need exists within the paper industry for a highly reliable and continuous optical property monitor coupled with a closed loop computer control system.

The value of such closed loop control, based on a feedback color detector, has already been demonstrated for the continuous addition of two and sometimes three dyes. (1) (2) Target dye concentrations changes of up to three dyes can be determined by solving three simultaneous equations containing three unknowns. (1) One disadvantage of such control is that accurate color monitoring is not presently available unless large and frequent empirically determined correction factors are applied to the original output results. A second disadvantage arises when opacity and the fluorescence must also be simultaneously controlled. In this case the number of independently controlled continuous additions increases from three to five. An optical brightener and an opacifying pigment constitute the two additional factors.

An object of this invention is to demonstrate a method by which fluorescence can be continuously monitored. A means by which the optical brightener addition can be separately and independently controlled is inherently implied. The paper color is also analyzed without the fluorescent contribution. It is, of course, this latter characterization (without fluorescence) which should be, but which has not in the past been, used to determine the required addition of the conventional dyes. In other words, the effect of the optical brightener is decoupled from the three conventional dyes making possible the simultaneous control of all four dyes.

Another portion of this invention demonstrates a means of continuously determining the scattering coefficient of the moving web for each of the six available light spectrums. It is possible to determine the scattering coefficient required to achieve a given opacity specification whenever the basis weight and absorption coefficient are known. When the latter are set equal to a given set of product specifications, then the calculated scattering coefficient becomes the target scattering coefficient. (The absorption coefficient can be acquired by off-line testing of a sample of the standard color to be matched. In reality, this becmes a target absorption coefficient as well.) The dyes have little, if any, effect on the scattering coefficient but the effect of the slurry pigment is very large. Thus the target scattering coefficient is used as the sole feedback variable to control the slurry pigment feed. This will insure that the opacity is at or near the specification as long, as the absorption coefficient and basis weight are also on target. The absorption coefficient should, of course, be on target by virtue of the independent color control. A completely independent system controls the basis weight.

A method by which the decoupling of three conventional dyes, one optical brightener and one opacifying pigment has hereby been explained. Heretofore, such decoupling as revealed in the prior art has been limited to three absorptive dyes and thereby neglecting the need to also achieve a specified degree of fluorescence and opacity.

References

1. The development of dynamic color control on a paper machine by H. Chao and W. Wickstrom; Automatica, Vol. 6 PP 5-18, Pergamon Press, 1970.
2. Another consideration for color and formation by Henry H. Chao and Warren A. Wickstrom, color engineering, September/October 1971.

I claim as my invention:

1. Apparatus for obtaining a quantitative measure of a paper optical property, which optical property is defined on the basis of reflectance measurement alone with specified backing and with respect to a given spectral response function of substantial bandwidth, said apparatus comprising:
   (a) an optical measuring device having a receiving region for receiving in operative relation thereto a single thickness of paper sheet material,
   (b) said optical measuring device having an optical system with at least two substantially independent photometric sensors and at least partly distinct light energy paths each including at least light source and spectral response filter means and a respective one of said photometric sensors, and each intersecting said receiving region prior to the respective associated photometric sensor,
   (c) each of said at least two distinct light energy paths having substantially a common spectral response characteristic sufficient to characterize said paper optical property and substantially corresponding to said spectral response function of substantial bandwidth, but being respectively arranged for collecting reflected and transmitted light energy from the receiving region after impingement of the light energy on a single thickness of paper sheet material at said region to provide reflectance and transmittance output signals, and (d) means (361, 370–377) connected with the photometric sensor (203) supplying said reflectance output signal for individually calibrating the same to provide a calibrated reflectance measurement correlated with an absolute reflectance of said paper sheet material, and means (429, 430–437) connected with the photometric sensor (260) supplying said transmittance output signal for individually calibrating the same to provide a calibrated transmittance measurement correlated with an absolute transmittance of said paper sheet material, with said calibrated reflectance and transmittance measurements together essentially characterizing the exclusively reflectance based paper optical property of the paper sheet material, whereby the paper optical property whose definition involves reflectance measurement alone is characterized with substantially greater accuracy than any characterization of said paper optical property by either a reflectance or a transmittance measurement on single thickness sheet material taken by itself.

* * * * *